US012458336B2

(12) United States Patent
Sauer et al.

(10) Patent No.: US 12,458,336 B2
(45) Date of Patent: Nov. 4, 2025

(54) STERNAL ASCENDER APPARATUS

(71) Applicant: LSI Solutions, Inc., Victor, NY (US)

(72) Inventors: Jude S. Sauer, Pittsford, NY (US); Matthew David DeClerck, Greece, NY (US); Angelo John Martellaro, Victor, NY (US); Benjamin James Boseck, Canandaigua, NY (US); Matthew Wrona, Fairport, NY (US)

(73) Assignee: LSI Solutions, Inc., Victor, NY (US)

( * ) Notice: Subject to any disclaimer, the term of this patent is extended or adjusted under 35 U.S.C. 154(b) by 324 days.

(21) Appl. No.: 18/110,619

(22) Filed: Feb. 16, 2023

(65) Prior Publication Data

US 2023/0200797 A1 Jun. 29, 2023

Related U.S. Application Data

(63) Continuation-in-part of application No. 16/999,838, filed on Aug. 21, 2020, now Pat. No. 11,666,317.

(60) Provisional application No. 62/889,690, filed on Aug. 21, 2019, provisional application No. 62/916,591, filed on Oct. 17, 2019, provisional application No. 62/989,044, filed on Mar. 13, 2020, provisional application No. 63/311,320, filed on Feb. 17, 2022.

(51) Int. Cl.
*A61B 17/02* (2006.01)

(52) U.S. Cl.
CPC ...... *A61B 17/0281* (2013.01); *A61B 17/0218* (2013.01); *A61B 2017/0237* (2013.01)

(58) Field of Classification Search
CPC .................... A61B 17/0281; A61B 2017/0237
See application file for complete search history.

(56) References Cited

U.S. PATENT DOCUMENTS

| | | | | |
|---|---|---|---|---|
| 1,919,455 A | | 7/1933 | Wilson | |
| 3,196,865 A | | 7/1965 | Rose | |
| 4,726,356 A | * | 2/1988 | Santilli | A61B 17/0206 600/234 |
| 4,829,985 A | * | 5/1989 | Couetil | A61B 17/0206 600/234 |
| 5,052,373 A | | 10/1991 | Michelson | |
| 5,167,223 A | * | 12/1992 | Koros | A61B 17/0206 600/234 |
| 5,772,583 A | * | 6/1998 | Wright | A61B 17/0206 600/234 |

(Continued)

OTHER PUBLICATIONS

PCT Search Report and Written Opinion for PCT/US2020/47440, International filing date Aug. 21, 2020, 9 pages, mailed Feb. 10, 2021.

(Continued)

*Primary Examiner* — Nicholas W Woodall
(74) *Attorney, Agent, or Firm* — Michael E. Coyne

(57) ABSTRACT

A sternal elevator apparatus is disclosed. The sternal elevator may include a panel, a support beam traversing the panel, and a post coupled to a proximal end of the panel. The apparatus may also include an indicator handle coupled to the sternal elevator, an actuator drive pivotably coupled to the indicator handle, and a housing movably coupled to the actuator drive. The sternal elevator apparatus may have an actuator drive incorporating a linear rack. The housing further may include a cylindrical gear where the cylindrical gear is engaged with the linear rack.

7 Claims, 36 Drawing Sheets

(56) References Cited

U.S. PATENT DOCUMENTS

| | | | | | |
|---|---|---|---|---|---|
| 5,782,753 | A * | 7/1998 | DeFonzo | A61B 17/0281 600/210 |
| 5,795,291 | A | 8/1998 | Koros et al. | |
| 5,846,191 | A | 12/1998 | Wells et al. | |
| 6,042,542 | A | 3/2000 | Koros et al. | |
| 6,102,854 | A * | 8/2000 | Cartier | A61B 17/0206 600/210 |
| 6,206,828 | B1 * | 3/2001 | Wright | A61B 17/0206 600/233 |
| 7,909,846 | B1 | 3/2011 | Taylor et al. | |
| 8,974,381 | B1 | 3/2015 | Lovell et al. | |
| 9,113,853 | B1 | 8/2015 | Casey et al. | |
| 9,216,016 | B2 * | 12/2015 | Fiechter | A61B 17/0206 |
| 9,335,782 | B2 | 5/2016 | Koros et al. | |
| 2005/0148824 | A1 | 7/2005 | Morejohn et al. | |
| 2005/0159651 | A1 | 7/2005 | Raymond et al. | |
| 2007/0238932 | A1 | 10/2007 | Jones et al. | |
| 2010/0312069 | A1 | 12/2010 | Sutherland et al. | |
| 2017/0239048 | A1 | 8/2017 | Goldfarb et al. | |
| 2020/0015801 | A1 | 1/2020 | Sauer | |

OTHER PUBLICATIONS

Chanoit et al, Retraction mechanics of Finochietto-style self-retaining thoracic retractors, BioMedical Engineering OnLine, 18, Article No. 45, 35 pages, Jul. 19, 2021.
Extended European Search Report for EP Application No. 20855514.4, dated Jul. 4, 2023, 10 pages.

* cited by examiner

STERNAL ASCENDER APPARATUS

CROSS-REFERENCE TO RELATED APPLICATIONS

This application is a continuation-in-part application claiming priority to U.S. patent application Ser. No. 16/999,838, filed Aug. 21, 2020, which claims priority to each of U.S. Provisional Patent Application No. 62/889,690, filed Aug. 21, 2019, U.S. Provisional Patent Application No. 62/916,591, filed Oct. 17, 2019, and U.S. Provisional Patent Application No. 62/989,044, filed Mar. 13, 2020, each of which is hereby incorporated by reference in its entirety. This application also claims the benefit of U.S. Provisional Patent Application No. 63/311,320, filed Feb. 17, 2022, which is hereby incorporated by reference in its entirety.

FIELD

The claimed invention relates to minimally invasive surgical devices, and more specifically to a surgical device used in increasing operable space during minimally invasive surgical procedures.

BACKGROUND

Minimally invasive surgical approaches are gaining increased interest in relation to coronary procedures. Coronary revascularization procedures such as the grafting of the internal thoracic artery (ITA) has shown superior long-term patency and improved patient outcome in coronary artery bypass graft (CABG) surgeries. While conventional approaches to ITA harvesting have included median sternotomy or multiple thoracoports, a minimally invasive approach is desirable. A minimally invasive procedure related to revascularization using either the left or right internal thoracic artery (ITA), or the left or right internal mammary artery (IMA) may utilize access to the ITAs via sub-xiphoid access, where increased surgical space is gained by accessing the internal thoracic arteries via incision at the subxiphocostal region.

Upon harvesting either the left internal thoracic artery (LITA) or the right internal thoracic artery (RITA) anastomoses to the left anterior descending (LAD) coronary artery and to the right coronary artery (RCA), respectively, can be performed without cardiopulmonary bypass (CPB). A significant advantage of this approach is that a perfectly harvested ITA graft can be perfectly anastomosed to the usual site on the LAD artery, or onto the RCA artery. A minimally invasive ITA harvesting procedure involving sub-xiphoid access also results in superior cosmetic results, is reasonably painless, and the arterial grafting can be accomplished on the beating heart. Recent approaches of minimally invasive ITA harvesting surgical techniques have been shown to result in increased effective length of ITA bypasses, reduced operation times, and improved patient recovery.

While less invasive surgical approaches for ITA harvesting and CABG have shown promise, visualization, maintenance of insufflation, and distal suturing of a coronary anastomosis in totally endoscopic coronary artery bypass grafting on the beating heart is technically demanding. There is a need for larger working spaces to accommodate an increased range of motion during surgical procedures, as well as room for additional surgical tools, such as endoscopes, suturing tools, and the like. However, achieving an increased working space should ideally preserve chest wall integrity and avoid CPB. Likewise, a minimally invasive surgical approach should not compromise the reliability of a cardiac repair.

Therefore, there exists a need for minimally invasive surgical devices and methodology applicable to ITA harvesting and other surgical procedures such as epicardial lead placement and others that increase operable space for harvesting and anastomosis and other surgical procedures, reduce operating time, and improve patient outcome during minimally invasive cardiac procedures and other surgical procedures.

Figure 1:
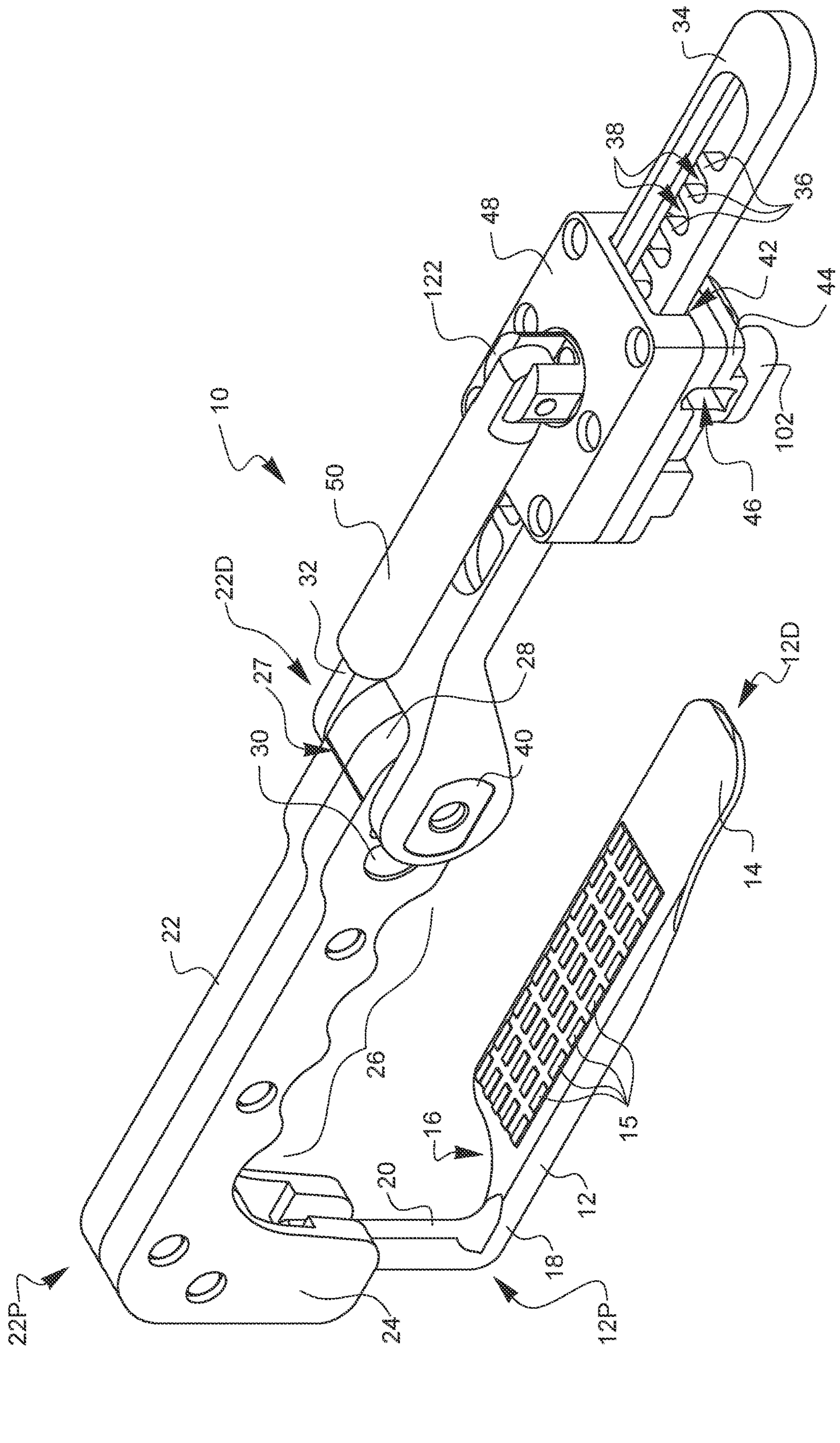
FIG. 1 is a top-front-right perspective view of one embodiment of a sternal ascender apparatus with a right sternal ascender attached.

It will be appreciated that for purposes of clarity and where deemed appropriate, reference numerals have been repeated in the figures to indicate corresponding features, and that the various elements in the drawings have not necessarily been drawn to scale in order to better show the features.

SUMMARY

A sternal ascender apparatus is disclosed. The sternal ascender may include a panel, a support beam traversing the panel, and a post coupled to a proximal end of the panel. The apparatus may also include an indicator handle coupled to the sternal ascender, an actuator drive pivotably coupled to the indicator handle, and a housing movably coupled to the actuator drive. The sternal ascender apparatus may have an actuator drive incorporating a linear rack. The housing further may include a cylindrical gear where the cylindrical gear is engaged with the linear rack.

Another sternal ascender apparatus is disclosed. The sternal ascender may include a panel having a plurality of textural features, a support beam traversing the panel, and a post coupled to a proximal end of the panel. The apparatus may also include an indicator handle removably coupled to the sternal ascender, an actuator drive pivotably coupled to the indicator handle having a linear rack, and a housing movably coupled to the actuator drive having a cylindrical gear and two instrument adapters.

DETAILED DESCRIPTION

FIG. 1 is a perspective view of one embodiment of a sternal ascender apparatus with a right sternal ascender attached. An embodiment of a sternal ascender apparatus 10 is shown in FIG. 1, with a right sternal ascender 12 installed therein. The right sternal ascender 12 defines a panel 14, the panel 14 having several textural features 15 configured to provide an atraumatic yet firm grip on the underside of a ribcage when the sternal ascender assembly 10 is in use in a minimally invasive surgical procedure. The panel 14 of the right sternal ascender 12 also defines a notch 16 and has a support beam 18 on the underside of the panel 14 The right sternal ascender 12 has a mounting post 20 on a proximal end 12P. The mounting post 20 is coupled to a proximal end 22P of an indicator handle 22 at the end of the mounting portion 24 of the indicator handle 22. The right sternal ascender 12 is coupled by reversible means such that the right sternal ascender 82 may be easily removed and replaced with a left sternal ascender, which is not shown in this view. The term ascender may be used interchangeably with the term elevator or lifter, as they equivalently describe the intended function of the ascender and associated apparatus. This coupling means will be described in further detail later. One alternate example of a coupling method is using a set screw, although others may be known to those skilled in the arts. The indicator handle 22 further defines a grip 26 in the underside of the indicator handle 22, which is configured for an ergonomic gripping feature for the comfort of use by a surgeon. At a distal end 22D of the indicator handle 22 is a connection end 28 and a pressable switch 30. Towards the distal end 22D of the indicator handle 22 is a depth indication mark 27, which is vertically aligned with the distal end 12D of the right sternal ascender 12. The connection end 28 is a coupling point that accepts a corresponding connection end 32 on a linear rack or linear actuator gear 34 by way of mating with the connection end 28 and is pivotably attached by joining a pivot pin 40 or alternatively by other attachment means into a hole or other attachment means not shown in this view. The pressable switch 30 can be pressed or actuated to defeat a pawl that is located inside the indicator handle 22, but not shown in this view. The pawl interfaces with a fixed indexing gear located inside the connection end 32 portion of the linear actuator gear 34. This will be discussed later in more detail in regard to FIGS. 2A-2E. The pawl defines a spring or biasing element to bias, while at rest, one or more teeth defined by the pawl toward the fixed indexing gear, which is not shown in this view but is coupled to the connection end 32 of the linear actuator gear 34. When the one or more teeth on the pawl intermesh with one or more corresponding teeth or other locking feature defined by the fixed indexing gear, this locks the angular position of the linear actuator gear 34 relative to the position of the indicator handle 22. When switch 30 is pressed or actuated, the pawl is defeated and temporarily pushed away from the fixed indexing gear, allowing free angular movement of the linear actuator gear 34 relative to the indicator handle 22. Releasing the switch 30, re-engages the pawl and the fixed indexing gear to once again interface and lock the angular position of the linear actuator gear 34 relative to the indicator handle 22 that it was in when the switch 30 was released.

The linear actuator gear 34 further defines several teeth 36 and several recesses 38 that engage a cylinder gear 122. The linear actuator gear 34 fits through an actuator slot 42 in a dual side instrument adapter 44. The dual side instrument adapter 44 defines a first adapter channel 46 and a second adapter channel, not visible here, on the opposite side. The dual side instrument adapter 44 also defines several locking mechanisms 100, 102 for locking the dual side instrument adapter 44 into a surgical equipment holder on each side. Once the dual side instrument adapter 44 is attached on each side to a surgical equipment holder, it can be positioned over a patient by bridging two surgical equipment holders across a surgical table. Other embodiments may only have a single adapter channel for mounting onto a single surgical equipment holder. Attached to the dual side instrument adapter 44 is a gear housing 48 which holds the cylinder gear 122. A handle or swivel bar 50 is coupled to the cylinder gear 122. Turning the handle 50 rotates the cylinder gear 122 and thereby moves the linear actuator gear 34 back and forth which forms an actuator drive. In this embodiment, the sternal ascender assembly 10 is inserted into an incision below the sub-xiphoid of a patient undergoing a minimally invasive surgical procedure, such as an ITA harvesting procedure or other surgical procedure in which increased access space below the sub-xyphoid process is advantageous. The panel 14 of the right sternal ascender 12 can be used to enable lifting the ribcage, thereby increasing space in the subxiphoid area. One feature of the sternal ascender assembly 10 is that the length of the distal end 22D of the indicator handle 22 is substantially the same as the length of the right sternal ascender 12 panel 14, which provides the surgeon with a visible indication, along with the depth indication mark 27 of how far the right sternal ascender 12 or the right sternal ascender (if installed into the sternal ascender apparatus 10) has been inserted into the subxiphoid cavity of the patient. The distal end 22D of the indicator handle 22 is substantially aligned with a distal end 12D of the sternal ascender 12. The indicator handle 22 is also substantially parallel to the panel 14 of the right sternal ascender 12 or the panel of a right sternal ascender. Once the sternal ascender apparatus or assembly 10 is inserted into the subxiphoid cavity, the sternal ascender assembly 10 is attached to one or more surgical equipment holders, enabling stability of force throughout a minimally invasive surgical procedure. Further adjustments to the position of the sternal ascender assembly 10 may then be made by pivoting about the coupling joint of the indicator handle 22 and the linear actuator gear 34. The sternal ascender assembly 10 can be further adjusted by rotating the swivel bar 50 and actuating the linear actuator gear 34 in a distal direction. This operation will be discussed in further detail later.

Figure 2A:
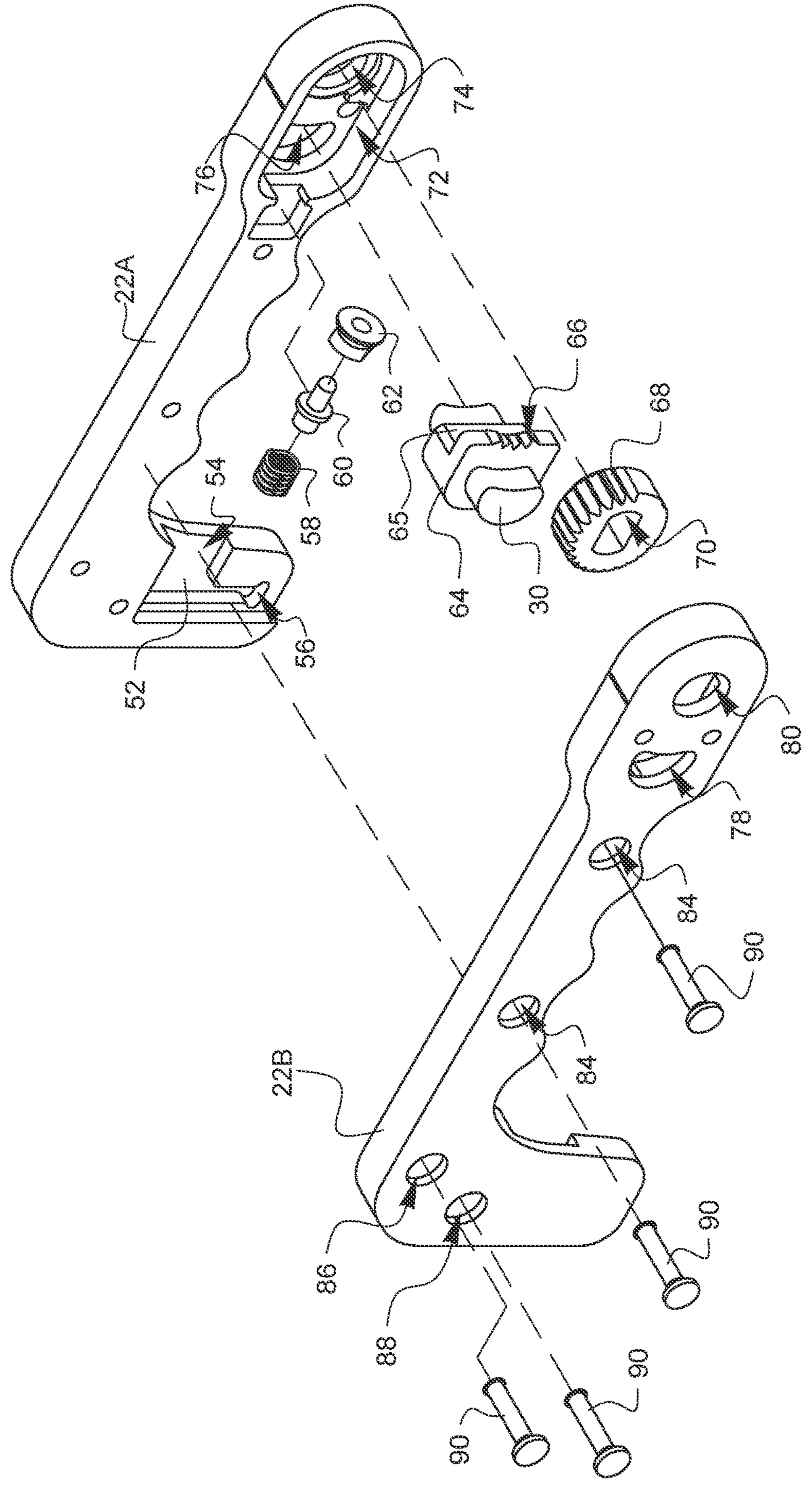
FIGS. 2A-2E is a series of exploded views illustrating the apparatus of the sternal ascender apparatus of FIG. 1.

FIGS. 2A-2E is a series of exploded views illustrating the assembly of the sternal ascender apparatus of FIG. 1. As illustrated in FIG. 2A, a first handle half 22A defines a recess or channel 52 having a mounting slot 54 and a seat 56. The mounting slot 54 and seat 56 defined by the channel 52, also referred to as a t-slot based on the general shape thereof, are configured to removably receive an alignment key on the post of either a left or right sternal ascender. A second handle half 22B also defines a corresponding recess, not shown in this view. The first handle half 22A also defines a second recess 72 at an opposite end and a gear recess 74 and hole 76. The second handle half 22B also defines a corresponding recess, not shown in this view. The second recess 72 is configured to receive and hold a spring 58, spring plunger 60, and plunger housing 62, which are first assembled together. A pawl gear 64 having gears 66 and an ungeared portion 65 and a fixed indexing gear or a pivot gear 68 having a gear keyway 70 are placed into hole 76 and held in gear recess 74, respectively, on the first handle half 22A. The pawl gear 64 is held against the spring 58, spring plunger 60, and plunger housing 62 assembly such that the pawl gear 64 is biased against the pivot gear 68 until the pawl gear 64 is depressed to slide the pawl gear 64 so that the gears 66 are disengaged from the pivot gear 68 such that it interfaces with the ungeared portion 65 of the pawl gear 64, thus allowing free rotation or pivoting of the pivot gear 68. When the pawl gear 64 is released, the gears 66 relock with the pivot gear 68 preventing further pivoting or rotation of the pivot gear 68. The second handle half 22B is then placed over the first handle half 22A and fastened using several rivets 90 which are placed and fixed into holes 84, 86, 88 on the second handle half 22B. While holes and rivets are used here to fixedly attach the handle halves 22A, 22B together, welding, adhesives or other means known to those skilled in the art may also be employed.

Figure 2B:
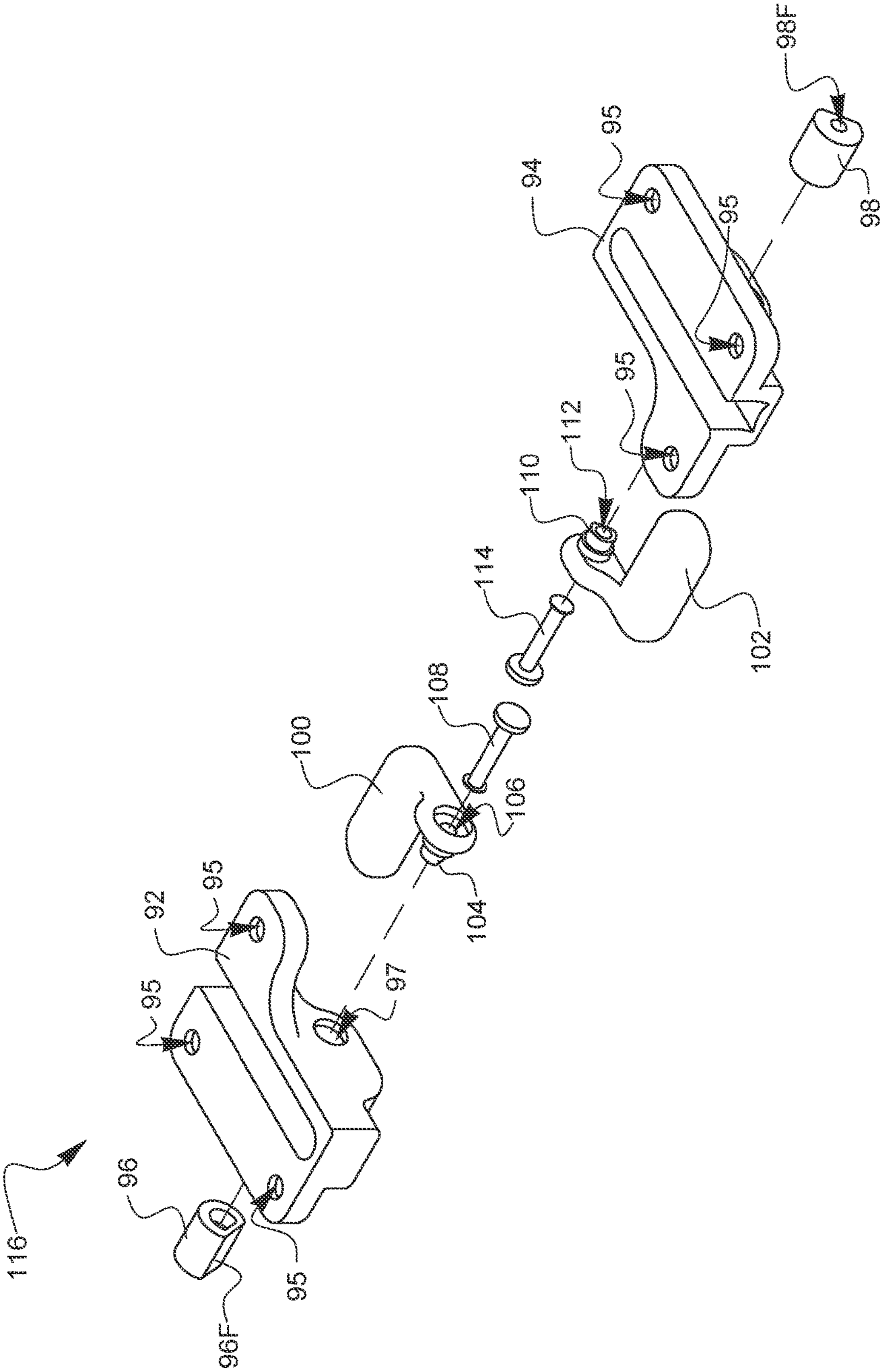

FIG. 2B illustrates the assembly of an instrument adapter assembly 116 portion of the sternal ascender apparatus 10. A first adapter housing 92 having several holes 95 and side hole 97 is assembled by placing a first cam 96 having a flat 96F into hole 97. A first lever lock 100 having a key 104 is placed into hole 97 and into the first cam 96 such that rotating the first lever lock 100 will also rotate the first cam 96 within hole 97. The first lever lock 100 is pivotably attached to the first adapter housing 92 with the use of rivet 108 being placed into channel 106 on the first lever lock 100. A second adapter housing 94 having several holes 95 and side hole, not visible here, is assembled by placing a second cam 98 having a flat 98F into hole 97. A second lever lock 102 having a key 110 is placed into a hole on the second adapter housing 94 and into the second cam 98 such that rotating the second lever lock 102 will also rotate the second cam 98 within the hole in the second adapter housing 94. The second lever lock 102 is pivotably attached to the second adapter housing 94 with the use of rivet 114 being placed into channel 112 on the second lever lock 102.

Figure 2C:
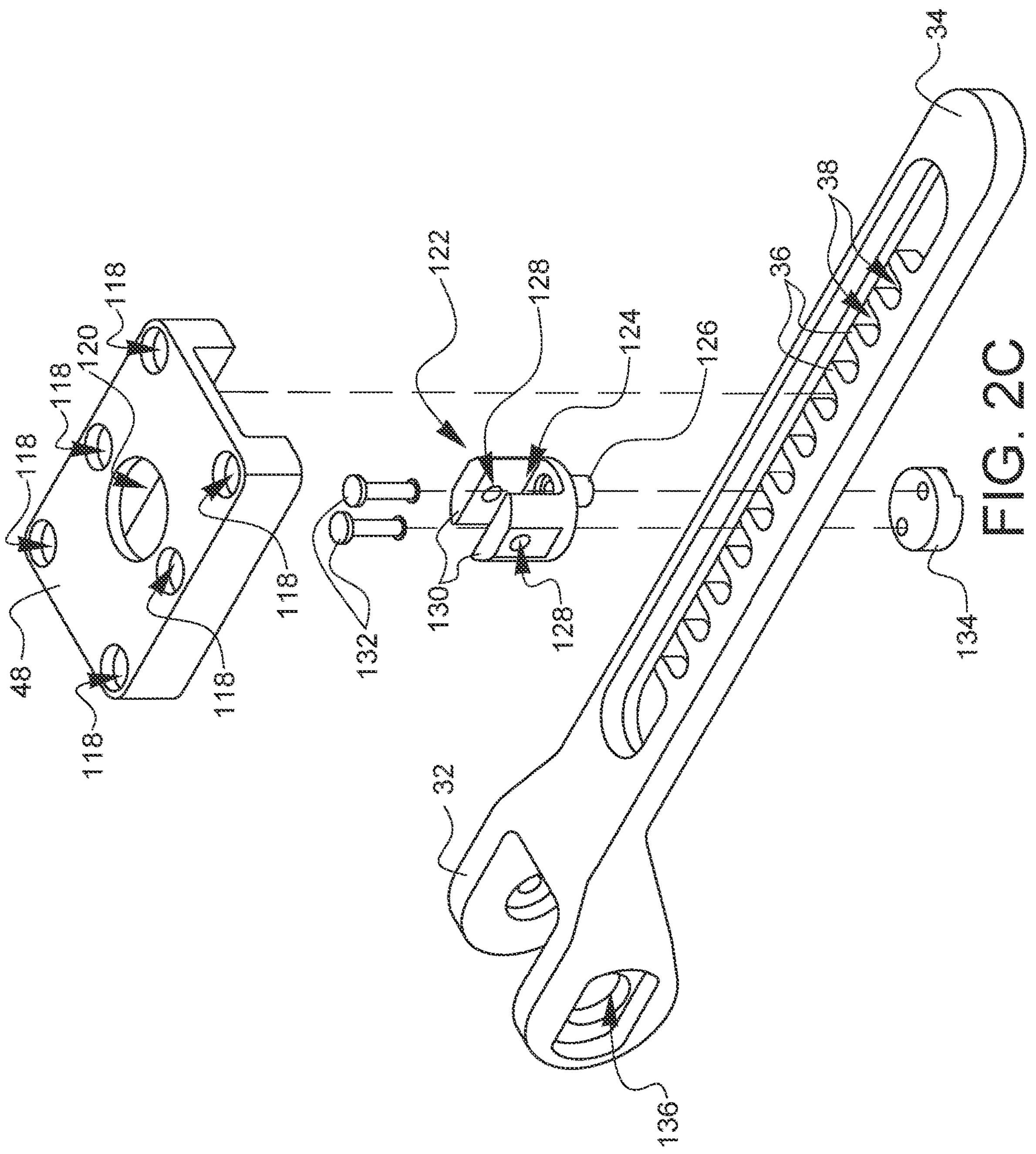
Figure 2D:
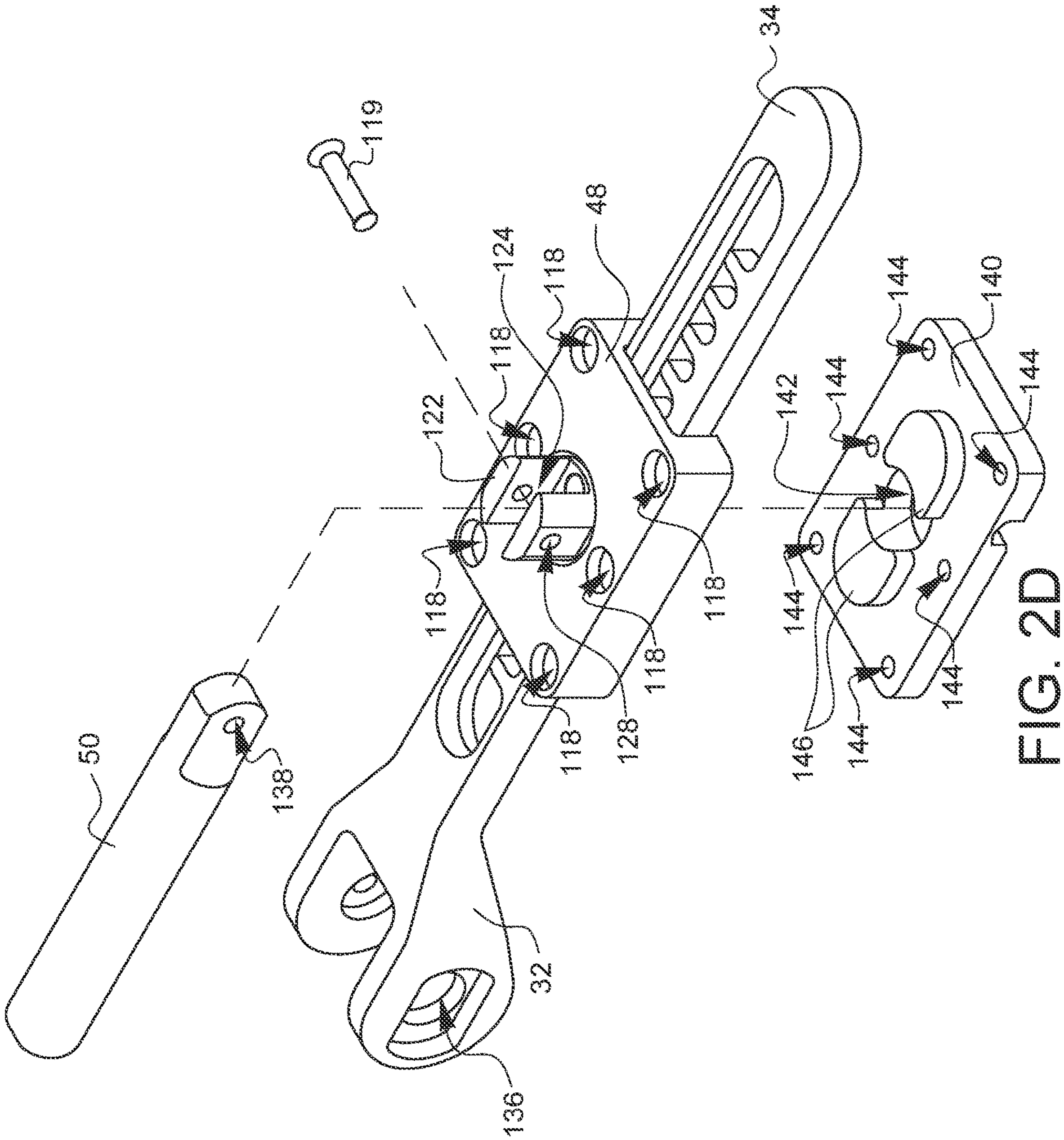
Figure 2E:
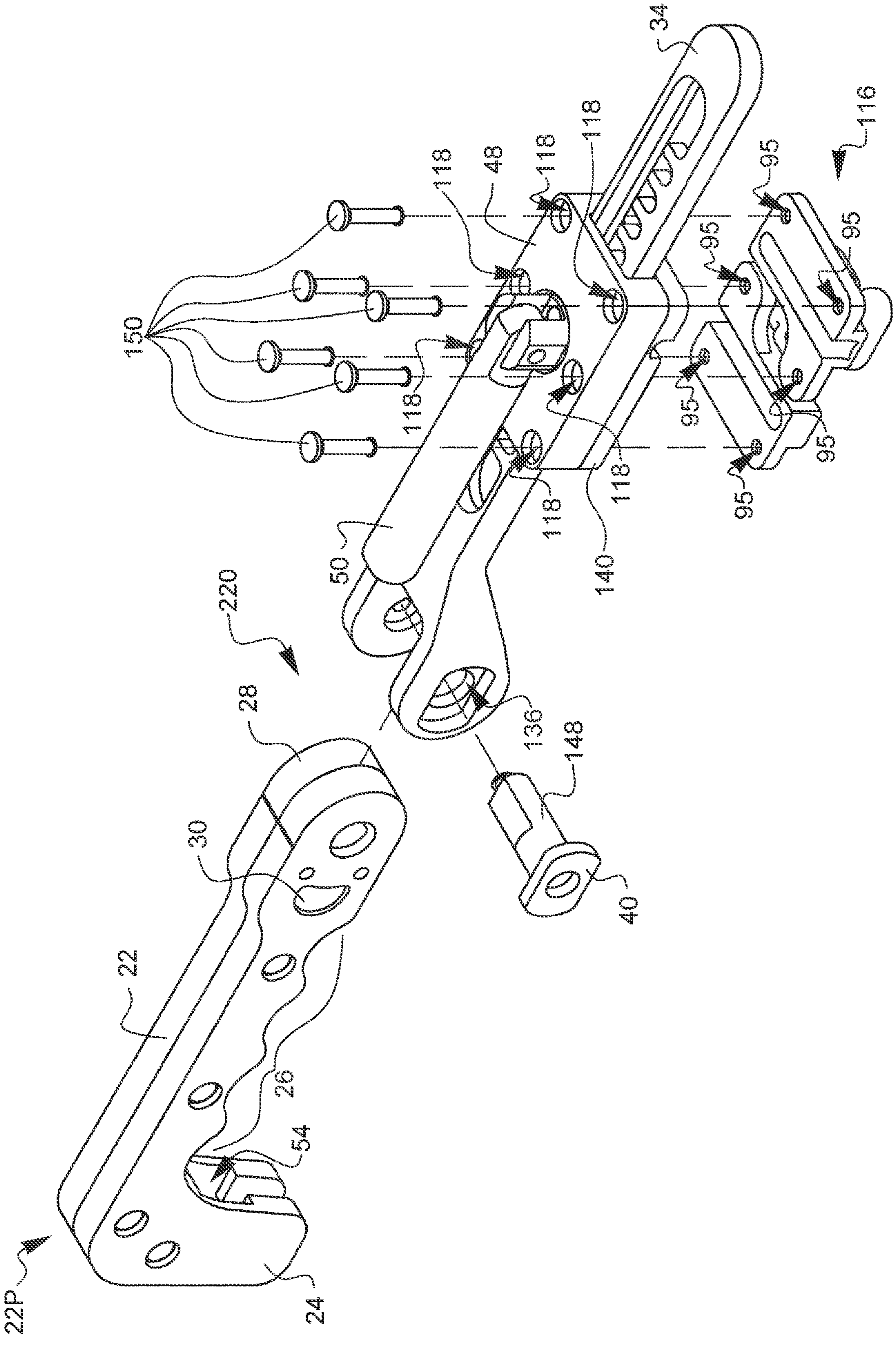

FIG. 2C continues the assembly of the sternal ascender apparatus 10 focusing on the linear actuator gear 34. The linear actuator gear 34, having a connection end 32 which further defines a hole 136 and several teeth 36 with several recesses 38 positioned therebetween. A cylinder gear 122 defines two sides 130, a side channel 128 on either side 130, a slot 124, and two posts 126, one of which is visible here, is placed into the linear actuator gear 34 with the two posts 126 held in two adjacent recesses 38. A drive bottom 134 is fixed with two rivets 132 onto the two posts 126 of the cylinder gear 122 on the opposite side of the linear actuator gear 34. Once fully assembled, the cylinder gear 122 is rotated in a clockwise or counterclockwise direction this thereby moves the linear actuator gear back and forth forming an actuator drive. As the cylinder gear 122 is rotated, the first pinion or post 126 will rotate out of a recess 38 on the linear actuator gear 34 and outward while the second pin driver (not visible here) remains in a second recess 38 and rotates within the second recess 38. The first post 126 will rotate into a third recess 38, past the second recess 38 thus translating rotational motion into linear motion and moving the linear actuator gear 34 relative to the gear housing 48. Performing this operation in the reverse will move the actuator gear 34 in the reverse direction. A upper rack housing 48 having a central opening 120 and several holes 118 is then placed over the linear actuator gear 34 and cylinder gear 122 so that the cylinder gear 122 protrudes from the central opening 120 of the upper rack housing 48 and the upper rack housing 48 is able to slide along the linear actuator gear 34 as the cylinder gear 122 is rotated. FIG. 2D illustrates the handle 50 being placed into the cylinder gear 122 between the two sides 130 and held in place by placing a rivet 119 through the side channels 128 on the cylinder gear 122 and through the hole 138 on the swivel bar 50. A middle rack housing 140 having a central hole 142, several holes 144, and two housing inserts 146 is placed onto the bottom of the linear actuator gear 34 to align with the upper rack housing 48. The holes 118 on the upper rack housing 48 are aligned with the holes 144 on the middle rack housing 140. The two housing inserts 146 are configured to hold captive and allow free rotation of the drive bottom 134 of the cylinder gear 122. The handle or swivel bar 50 is used to swivel and rotate the cylinder gear 122 during operation. The assembly of the sternal ascender apparatus 10 is completed in FIG. 2E by inserting the distal end 22D of the indicator handle 22 into the linear actuator gear 34. The pivot pin 40 is inserted into hole 136 with the pivot pin post 148 interlocking into the gear keyway 70 of the pivot gear 68, the function of which was illustrated in FIG. 2A. The instrument adapter assembly 116 shown and described in regard to FIG. 2B is placed onto the bottom of the middle rack housing 140 and holes 95 in the instrument adapter assembly 116 are aligned with the corresponding 118 holes in the upper rack housing 48. Several rivets 150 are then placed into the holes 118 to fixedly join the instrument adapter assembly 116 to the middle rack housing 140 and upper rack housing 48.

Figure 3:
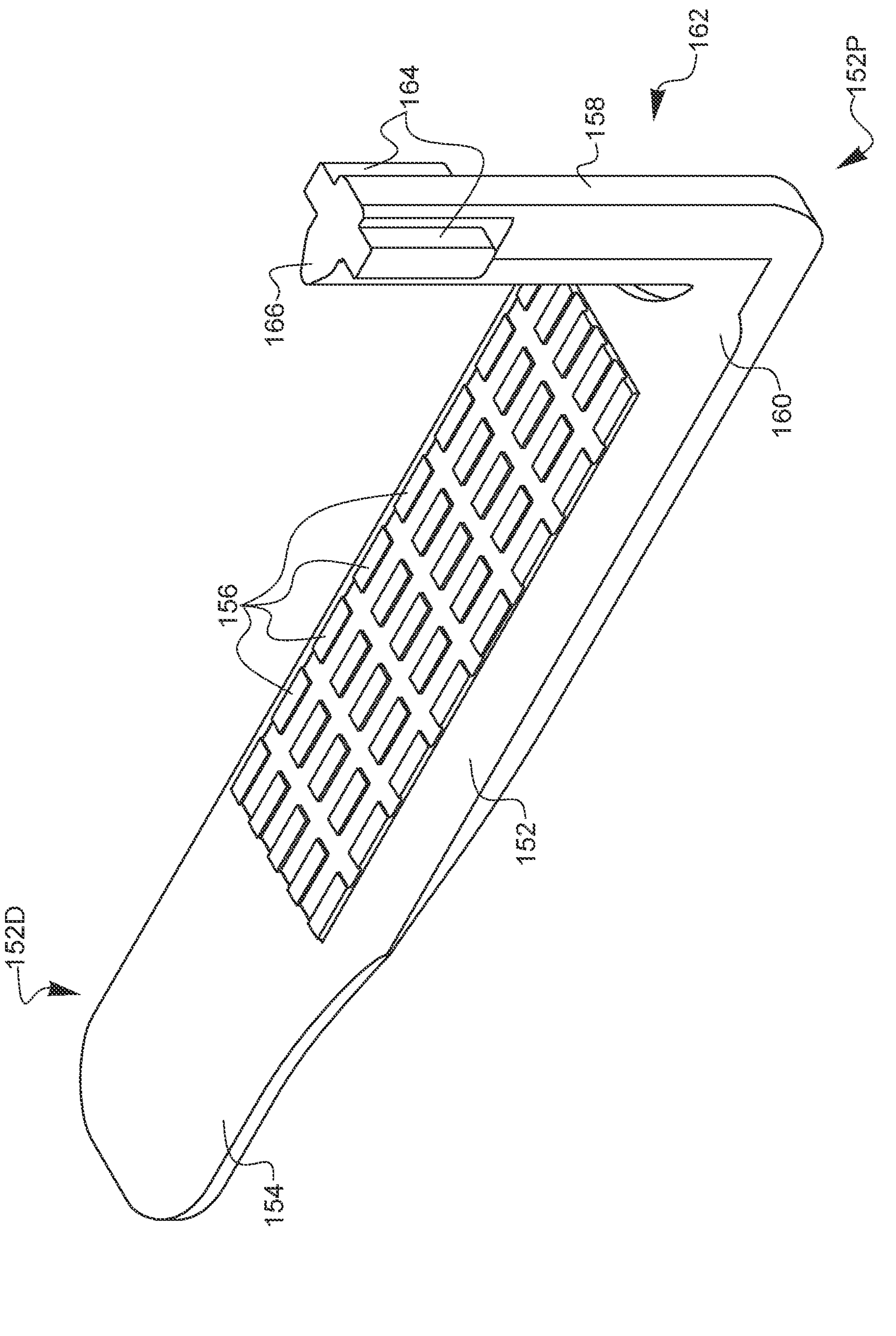
FIG. 3 is a perspective view of a left sternal ascender.
Figures 4A, 4B, 4C, 4D, 4E, 4F:
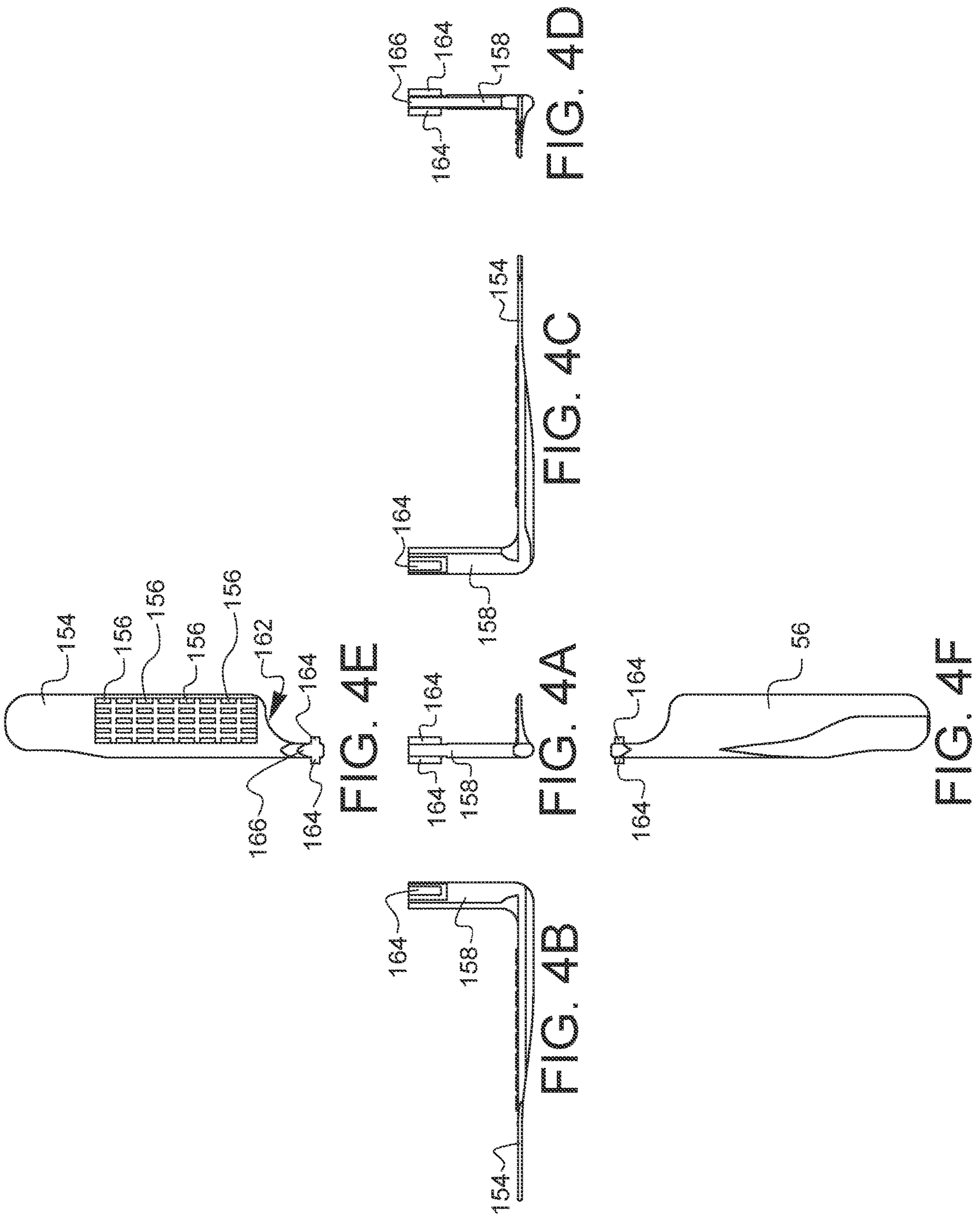
FIGS. 4A, 4B, 4C, 4D, 4E, and 4F are front, left side, right side, rear, top, and bottom elevational views, respectively, of the sternal ascender of FIG. 3.

FIG. 3 is a perspective view of a left sternal ascender. This view illustrates the various features defined by the left sternal ascender 152. The left sternal ascender 152 defines a panel 154 having several textural features 156, a contralateral, or pertaining to the opposite side of targeted anatomical area, notch 162 at a proximal end 152P, a support beam 160 traversing the underside of the panel 154, and a mounting post 158 for attachment to a sternal ascender apparatus. The panel 154 has a rounded shape with a slight edge at a distal end 152D of the panel 154 of the left sternal ascender 152. Also defined by the post 158 are two opposing alignment and orientation features 164 configured to align, slide and lock the left sternal ascender 152 into the handle. These features 164 form a general t-shape, which are configured to fit into the aforementioned t-slot on the indicator handle 22. The use of this feature will be described further in regard to FIGS. 7A-7C. The post 158 also defines an angular front alignment feature 166 which is used to help align and place the left sternal ascender in an anatomical notch defined between a rib and sternum. This can serve as a tactile assist in placing the sternal ascender in an appropriate place when in use as part of a sternal ascender apparatus. While the embodiment shown has these characteristics, alternate embodiments of a sternal ascender panel may have other shapes or radiuses, and may or may not be sharpened. Still other embodiments may have other features aside from the rectangular textural features 156 shown here, and may include other shaped features or none at all. Other embodiments of left sternal ascenders may be made of metal, plastic, composites, or mixtures or combinations thereof or contain alternate alignment or locking methods and features. FIGS. 4A, 4B, 4C, 4D, 4E, and 4F are front, left side, right side, rear, top, and bottom elevational views, respectively, of the sternal ascender of FIG. 3.

Figure 5:
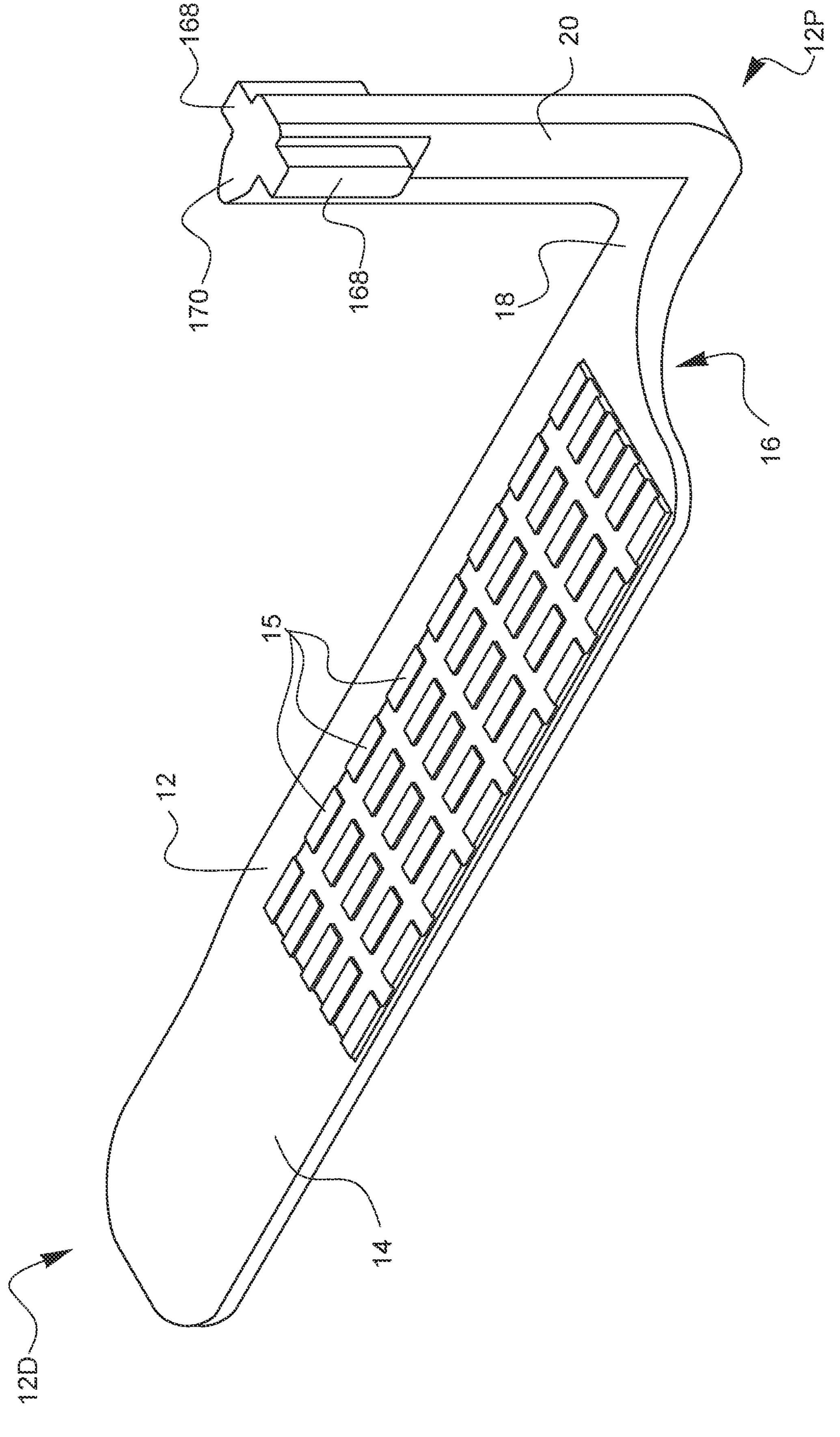
FIG. 5 is a perspective view of a right sternal ascender.
Figures 6A, 6B, 6C, 6D, 6E, 6F:
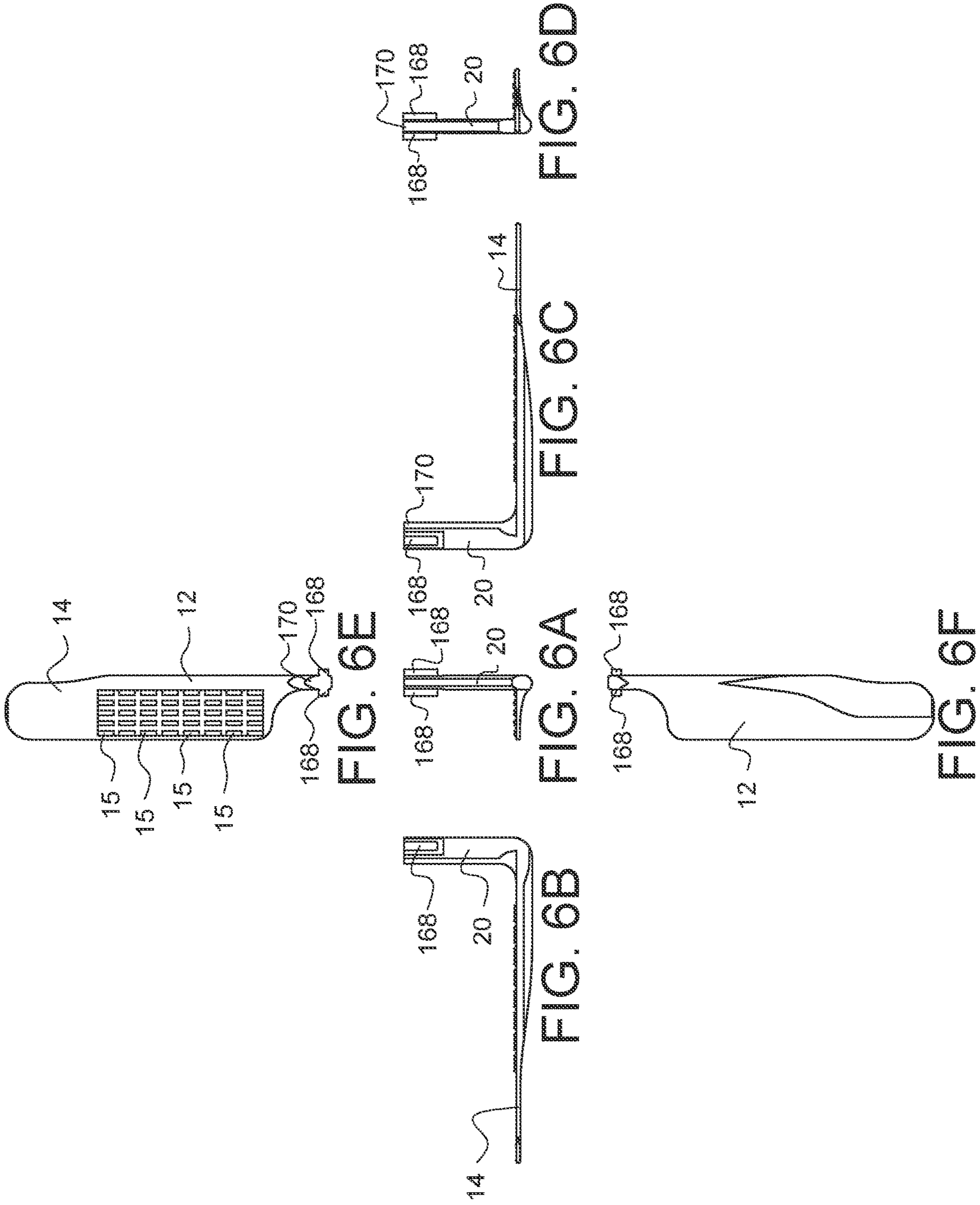
FIGS. 6A, 6B, 6C, 6D, 6E, and 6F are front, left side, right side, rear, top, and bottom elevational views, respectively, of the right sternal ascender of FIG. 5.

FIG. 5 is a perspective view of a right sternal ascender. This view illustrates the various features defined by the right sternal ascender 12. The right sternal ascender 12 defines a panel 14 having several textural features 15, a contralateral, or pertaining to the opposite side of targeted anatomical area, notch 16 at a proximal end 12P, a support beam, not shown here, traversing the underside of the panel 14, and a mounting post 20 for attachment to a sternal ascender assembly. The panel 14 has a rounded shape with a slight edge at a distal end 12D of the panel 14 of the right sternal ascender 12. Also defined by the post 20 are two opposing alignment and orientation features 168 configured to align, slide and lock the left sternal ascender 12 into the handle. These features 168 form a general t-shape, which are configured to fit into the aforementioned t-slot on the indicator handle 22. The use of this feature will be described further in regard to FIGS. 7A-7C. The post 20 also defines an angular front alignment feature 170 which is used to help align and place the left sternal ascender in an anatomical notch defined between a rib and sternum. This can serve as a tactile assist in placing the sternal ascender in an appropriate place when in use as part of a sternal ascender apparatus. While the embodiment shown has these characteristics, alternate embodiments may have other shapes or radiuses, and may or may not be sharpened. Still other embodiments may have other attachment features aside from the rectangular textural features 15 shown here, and may include other shaped features or none at all. Other embodiments of right sternal ascenders may be made of metal, plastic, composites, or mixtures or combinations thereof. FIGS. 6A, 6B, 6C, 6D, 6E, and 6F are front, left side, right side, rear, top, and bottom elevational views, respectively, of the right sternal ascender of FIG. 5.

Figure 7A:
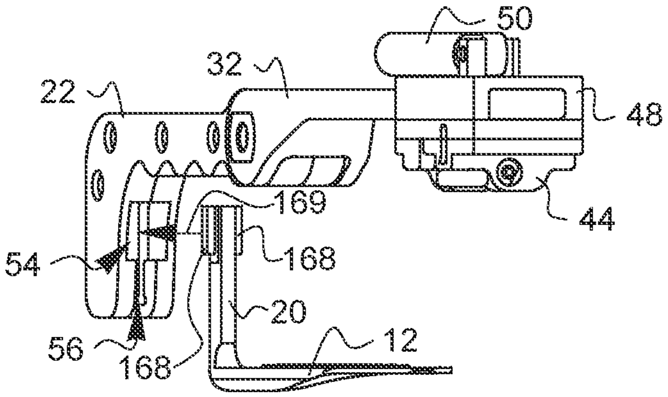
FIGS. 7A-7C are a series of perspective views illustrating operational steps showing the loading of the left sternal ascender of FIG. 5 into the sternal ascender apparatus of FIG. 1.
Figure 7B:
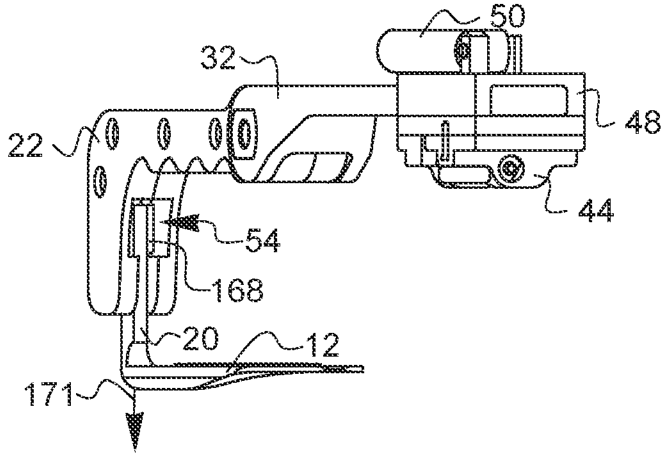
Figure 7C:
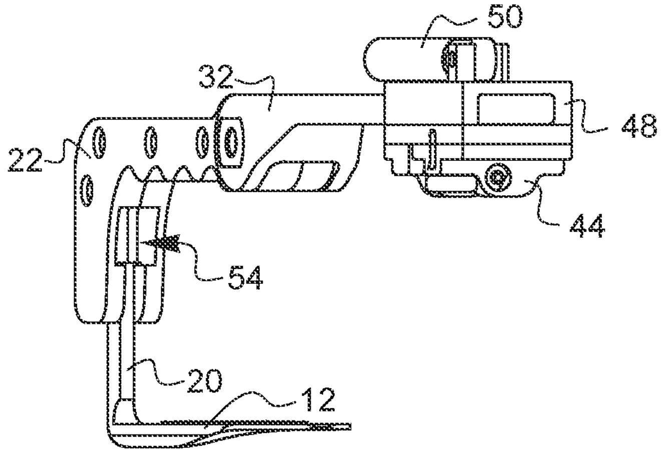

FIGS. 7A-7C are a series of perspective views illustrating operational steps showing the loading of the left sternal ascender of FIG. 5 into the sternal ascender apparatus of FIG. 1. The appropriate sternal ascender, left or right, is selected depending on the area of interest for a minimally invasive surgical procedure requiring the sternum of a patient to be lifted upward. FIG. 7A shows the right sternal ascender 12 aligned with and in proximity to the t-slot 54 of the indicator handle 22 of the sternal elevator apparatus 10 with the orientation features 168 on the post 20 of the right sternal ascender 12 moved towards direction 169 and fully inserted into the slot 54 of the indicator handle 22. Once inserted, as shown in FIG. 7B, the right sternal ascender 12 is pulled downward in direction 171 towards the seat 56 in the slot 54 of the indicator handle 22 to lock the right sternal ascender 12 into place. FIG. 7C shows the fully inserted and locked right sternal ascender 12 in the indicator handle 22.

Figure 8:
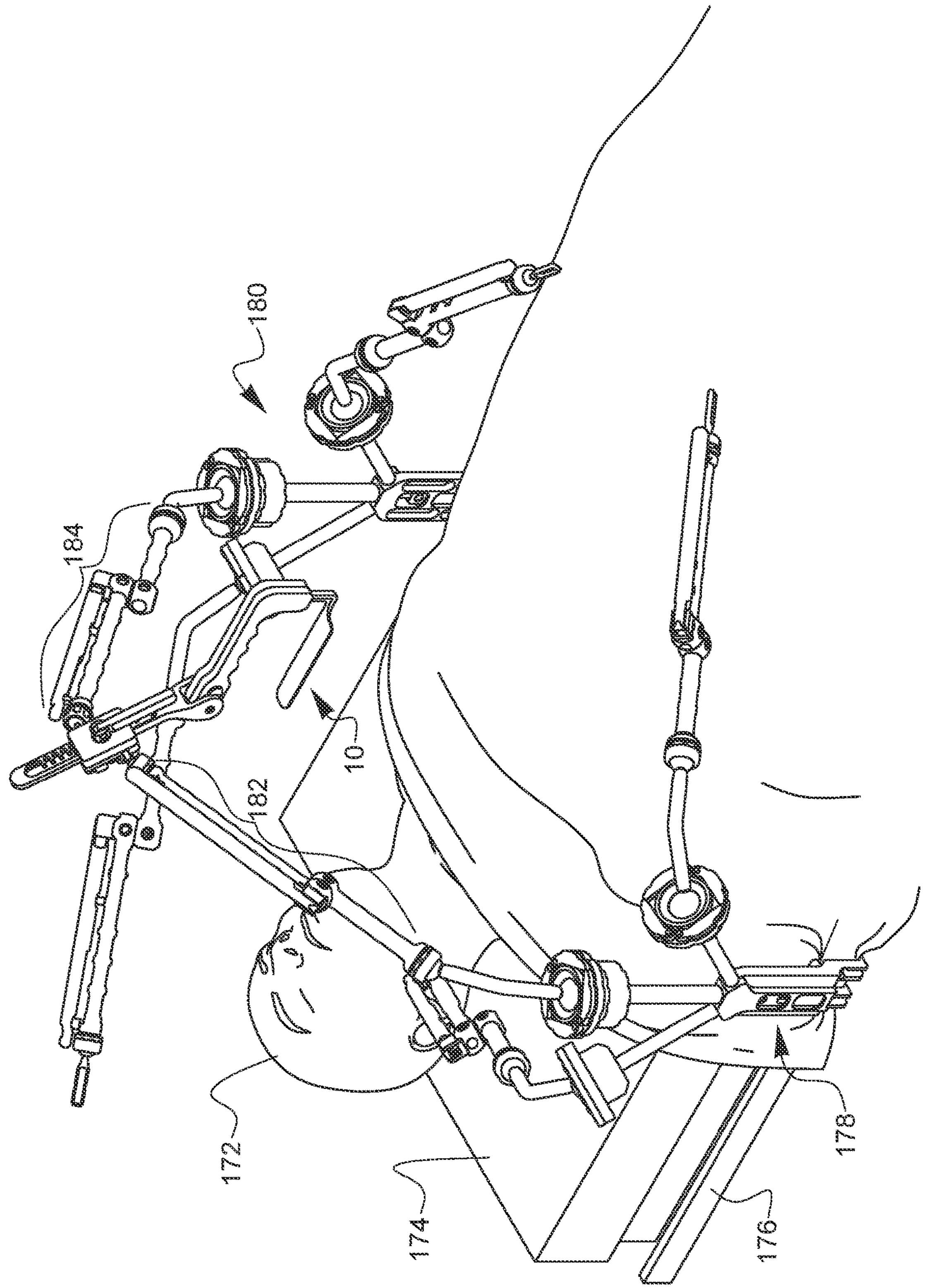
FIG. 8 is a perspective view of a surgical setting including the use of the sternal ascender apparatus of FIG. 1.

FIG. 8 is a perspective view of a surgical setting including the use of the sternal ascender apparatus of FIG. 1. In the illustrated surgical setting, an operating table 174 having a rail 176 and a patient 172 on the table 174 prepared for a surgical procedure are shown. Positioned on the rail 176 is a first surgical equipment holder apparatus 178 having a first central surgical equipment holder 182 attached to the first surgical equipment holder apparatus 178. The first surgical equipment holder apparatus 178 is attached to the sternal ascender apparatus 10 at the first adapter channel 46. On an opposite side of the table, a second surgical equipment holder apparatus 180 is attached to an opposite rail, which is not visible here. The second surgical equipment holder apparatus 180 has a second central surgical equipment holder 184 attached thereto and is also attached to the corresponding second adapter channel on the sternal ascender apparatus 10 on its opposite side, not visible here. Each of the first central surgical equipment holder 182 and the second central surgical equipment holder 184 can be utilized to position and hold one or more pieces of surgical equipment or tools such as the sternal ascender apparatus 10 or alternatively scope holders, cannulas, or other surgical implements during a minimally invasive or other surgical procedure. In this configuration, the first central surgical equipment holder 182 and the second central surgical equipment holder 184 are shown bridging over the patient 172 in order to firmly position the sternal ascender apparatus 10 in an initial centralized location relative to the patient 172 on the table 174.

Figure 9A:
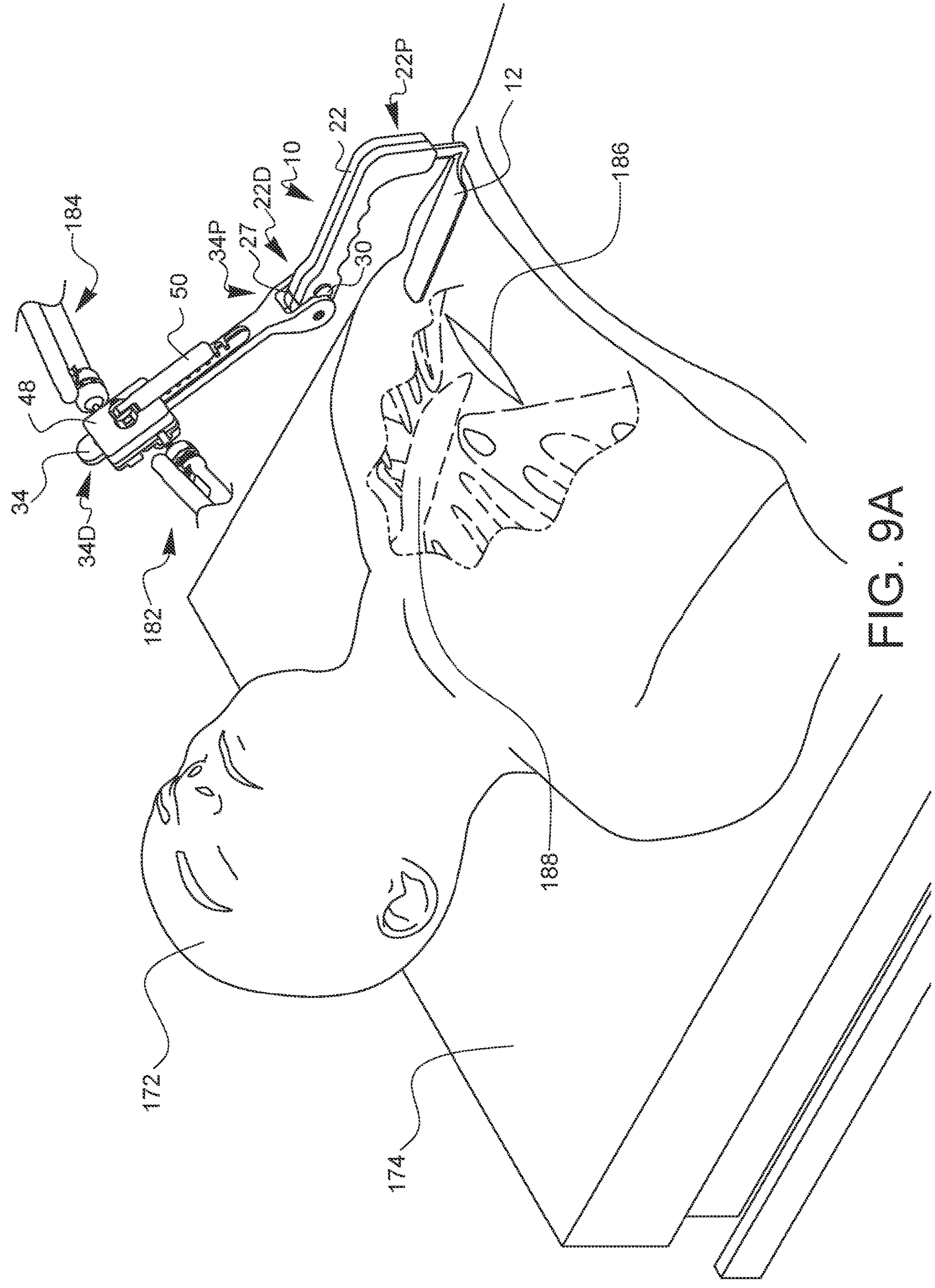
FIGS. 9A-9D are a series of perspective views illustrating operational steps of the use of the sternal ascender apparatus in a surgical context.
Figure 9B:
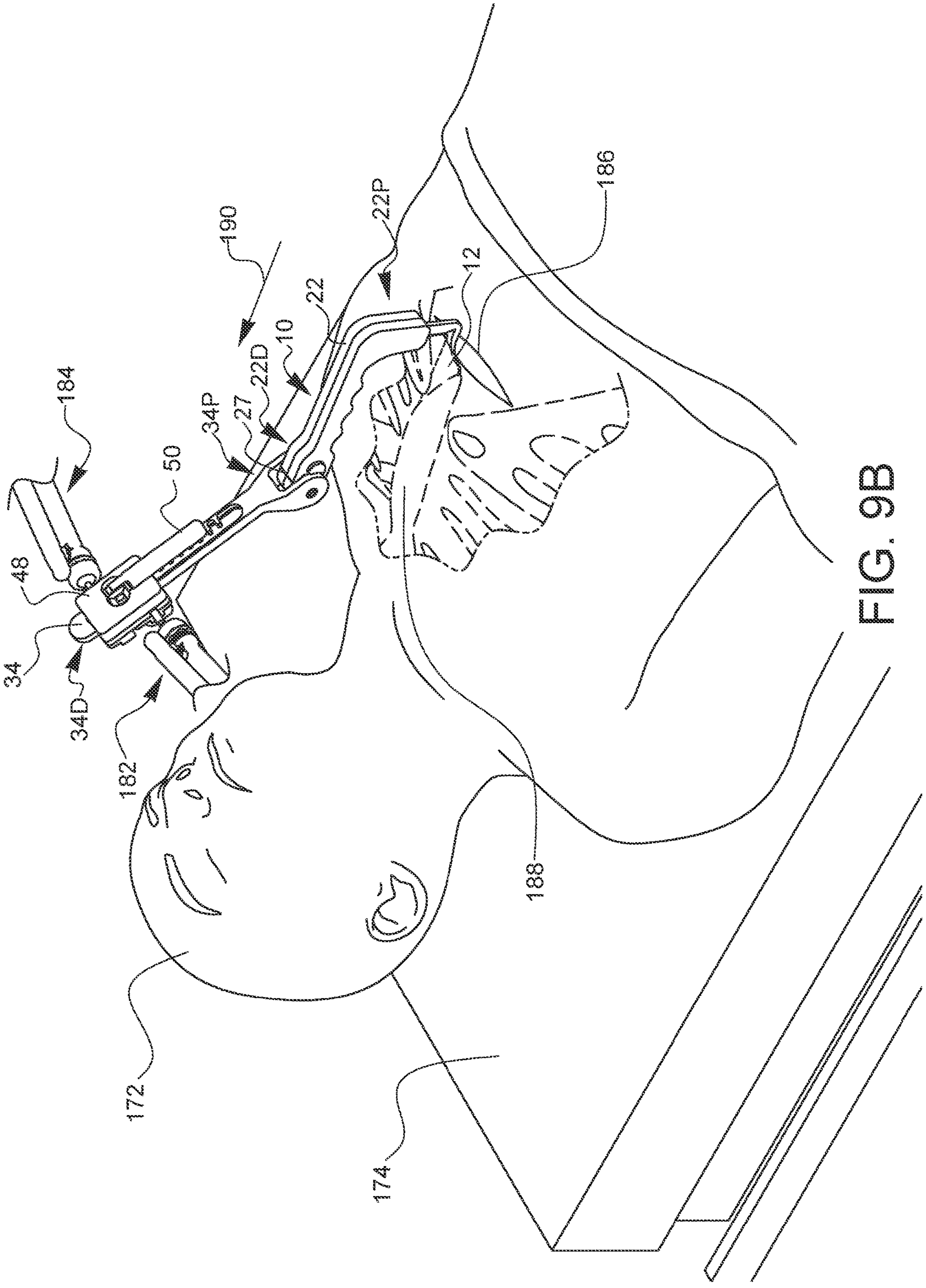
Figure 9C:
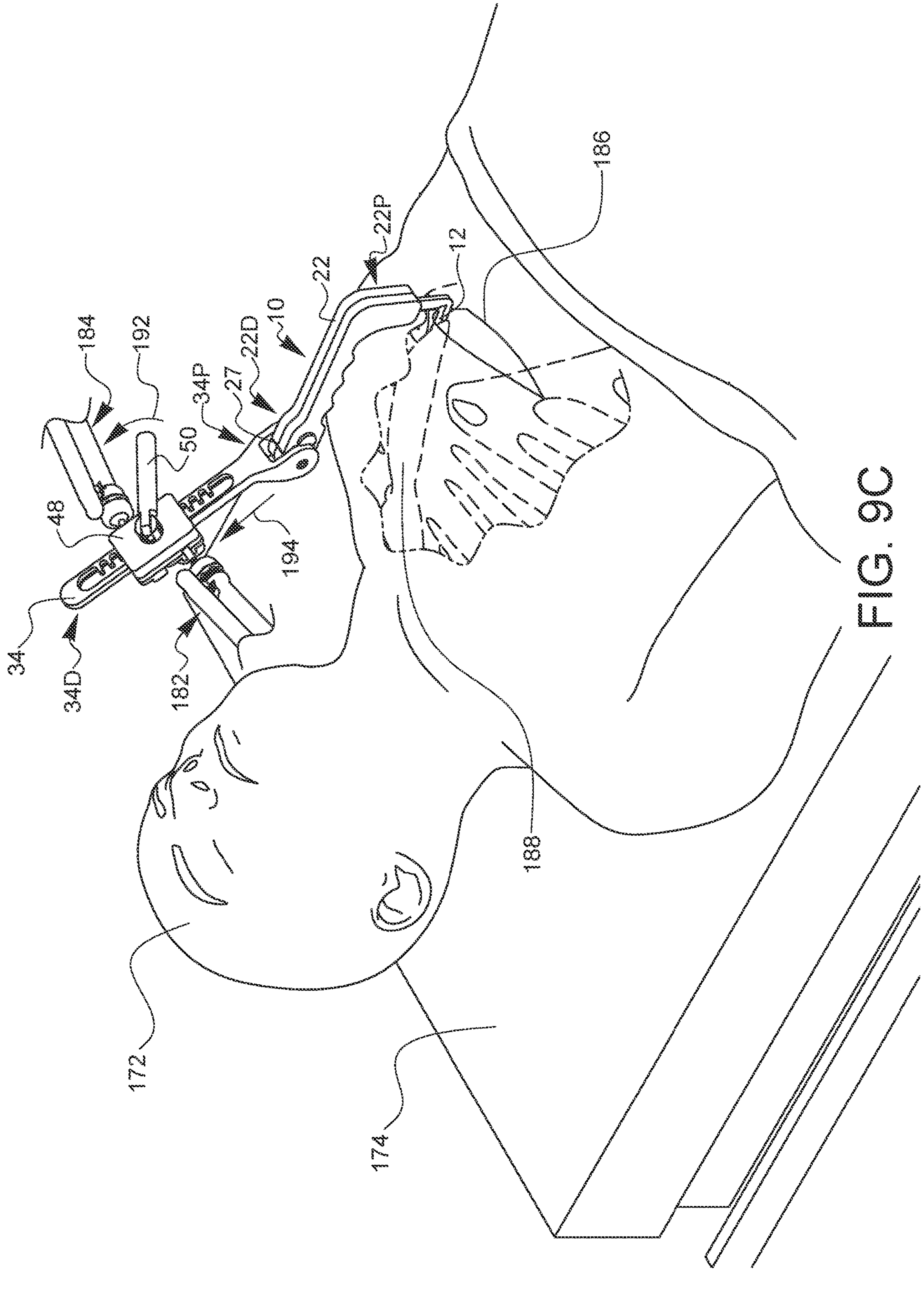
Figure 9D:
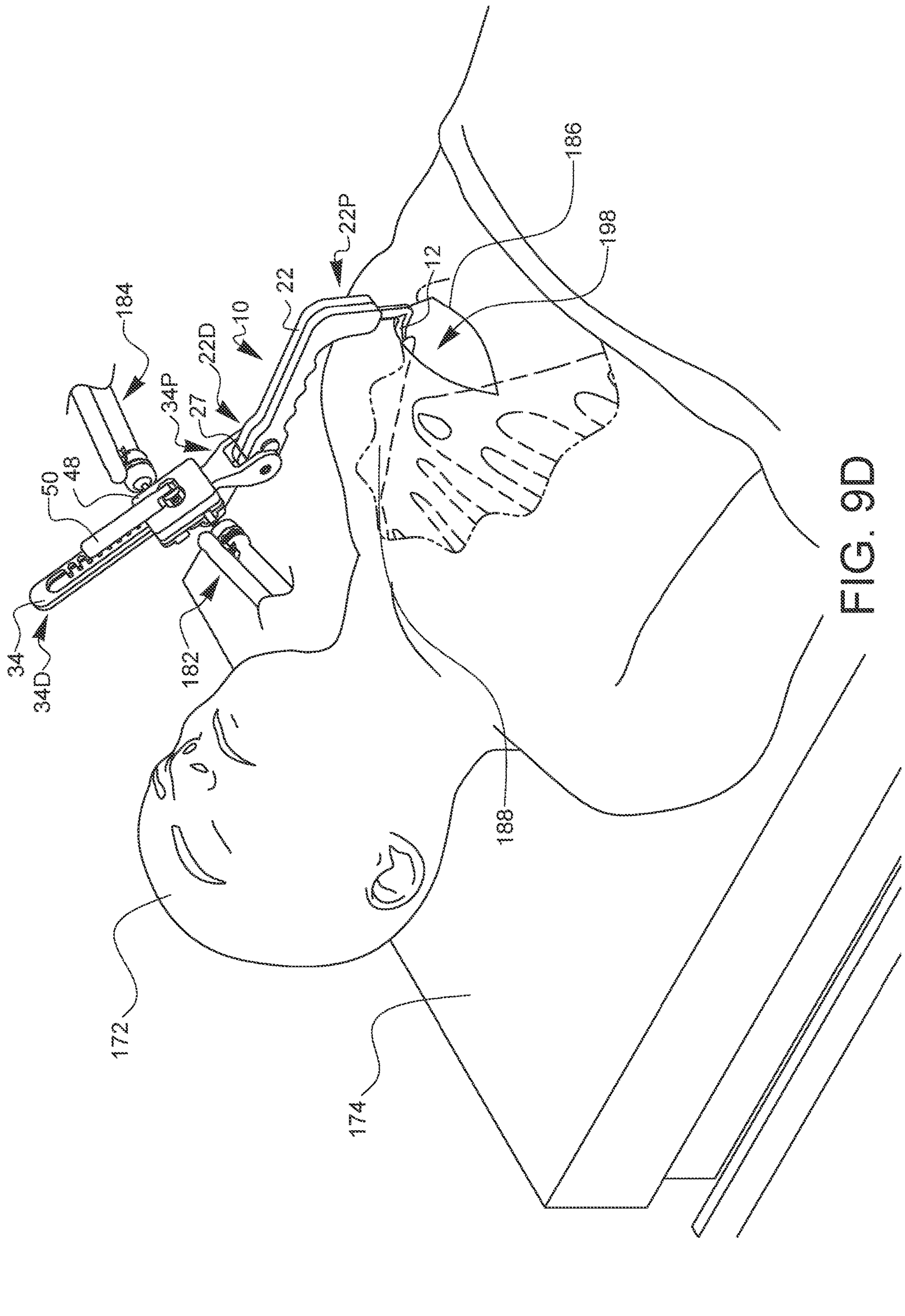

FIGS. 9A-9D are a series of perspective views illustrating operational steps of the use of the sternal ascender apparatus in a surgical context. In FIGS. 9A-9D, portions of the patient 172 are shown in cross-section and portions of various instrumentation are removed from view for the purposes of clarity. The patient 172 is shown prepped for a surgical procedure, having an incision 186 made at just below the xiphoid process at the sternal notch, near the sternum 188. The sternal elevator apparatus 10 is secured onto the first central surgical equipment holder 182 and the second central surgical equipment holder 184, which are firmly mounted onto the operating table 174. The upper rack housing 48, or the arch keystone is at the top of the toothed linear rack and thus enables subsequent movement of the rack 34 upward. The angle of the indicator handle 22 and therefore the sternal ascender 12 has been adjusted by pressing the pivot button or pressable switch 30 on the indicator handle 22, allowing movement of the indicator handle 22 relative to the linear actuator gear 34. As shown in FIG. 9B, the distal end 12D of the sternal ascender 12 is inserted in direction 190 into the incision 186 until the sternal ascender 12 is in a desired location along the sternum 188. The sternal ascender 12 is aligned with the anatomy of the sternum 188 by using the depth indicator 27 to gauge the location of the tip of the panel of the sternal ascender 12 within the chest. At this point, the first central surgical equipment holder 182 and the second central surgical equipment holder 184 are locked and secured into place after proper adjustment. FIG. 9C illustrates the swivel bar 50 being unlocked and moved counterclockwise 192 to raise the sternal ascender 12 and indicator handle 22 in direction 194, which applies retraction to the sternum 188 and creates the subxiphoid space 198 for access. A final state of this described procedure is illustrated in FIG. 9D, at which time the swivel bar 50 can be moved to a full up or down position to lock the gear housing 48 in place to prevent any further movement of the sternal ascender 12.

Figure 10A:
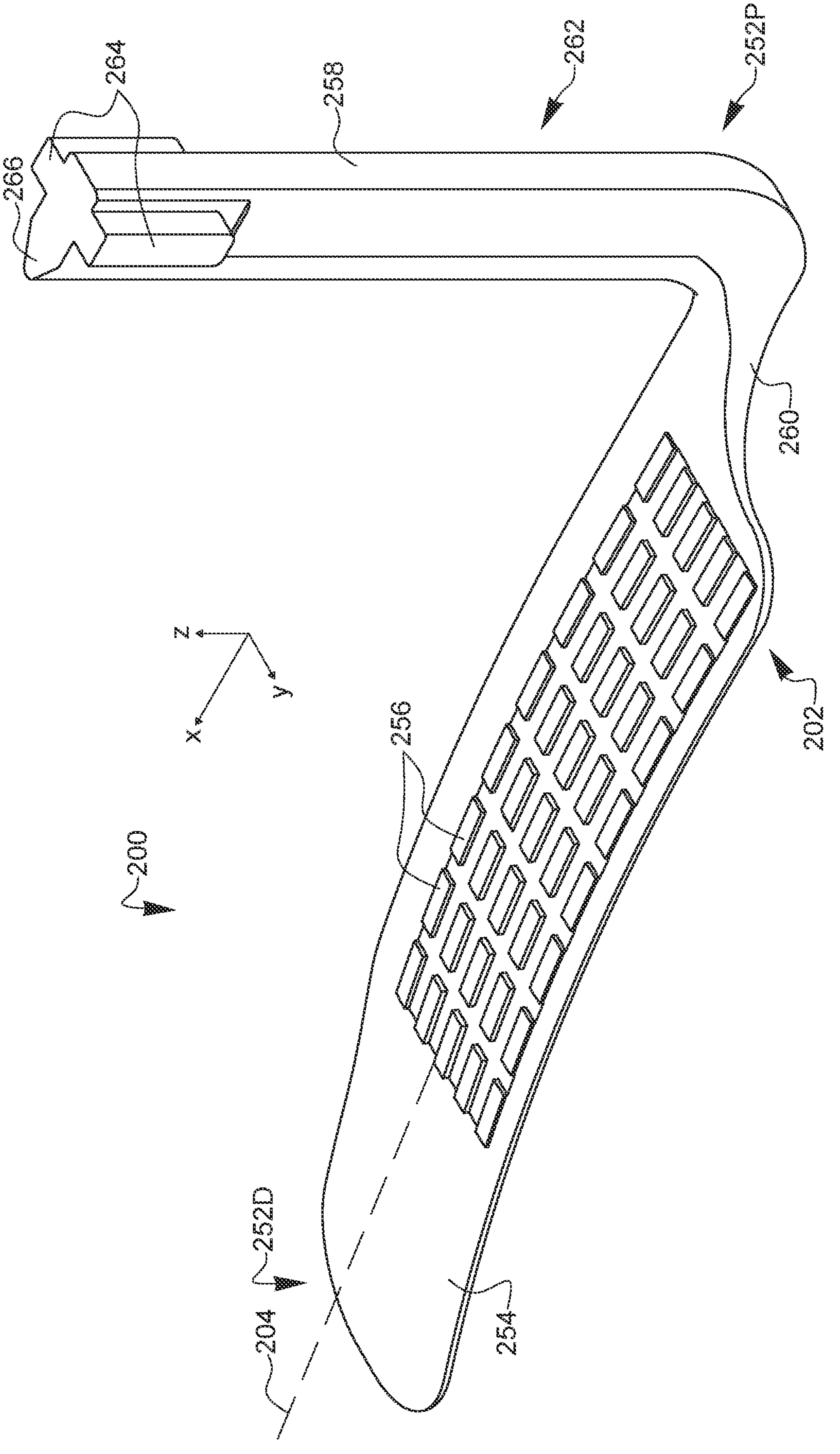
FIGS. 10A to 10G are various views of an embodiment of a right sternal ascender.
Figure 10B:
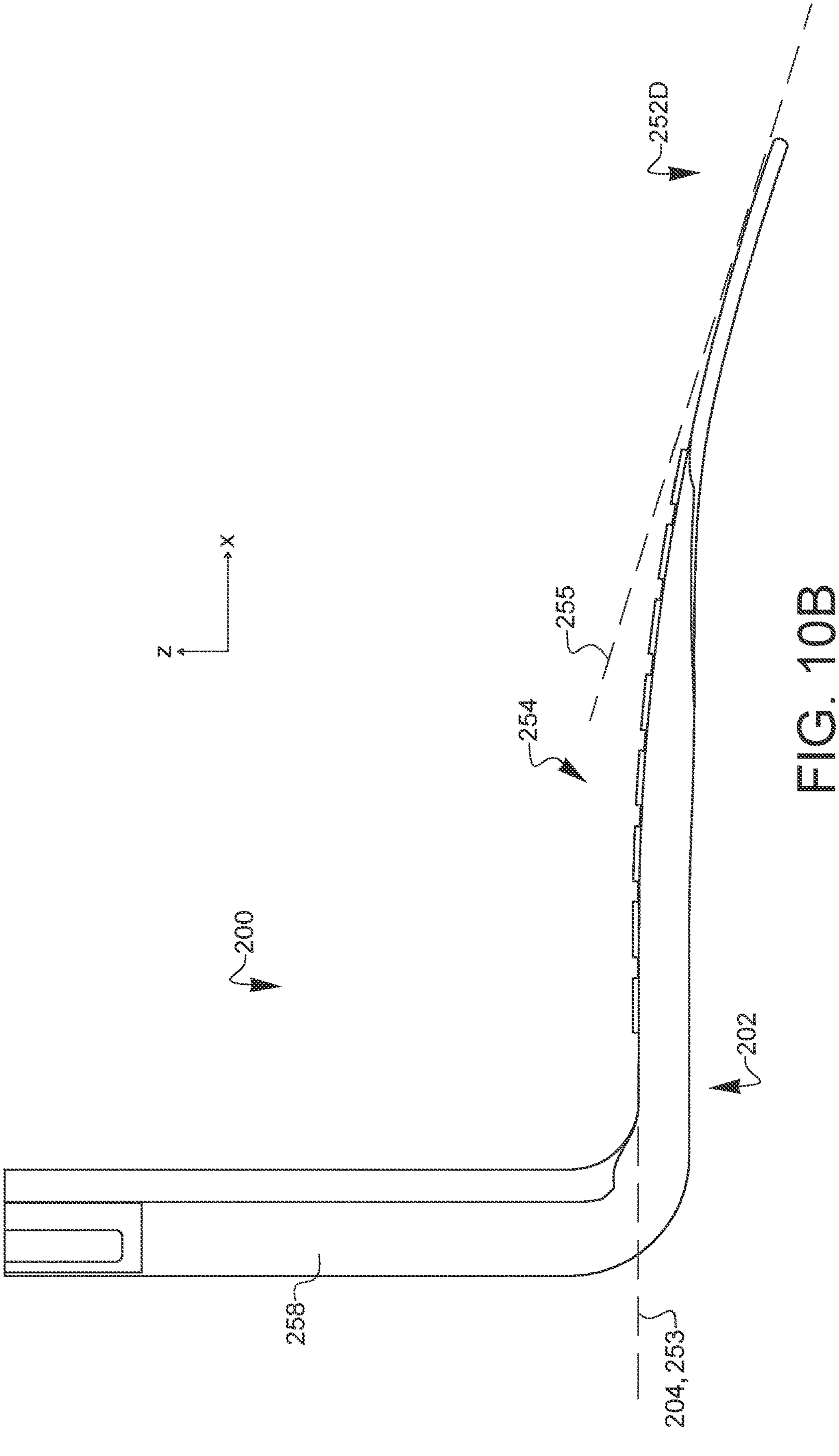
Figure 10C:
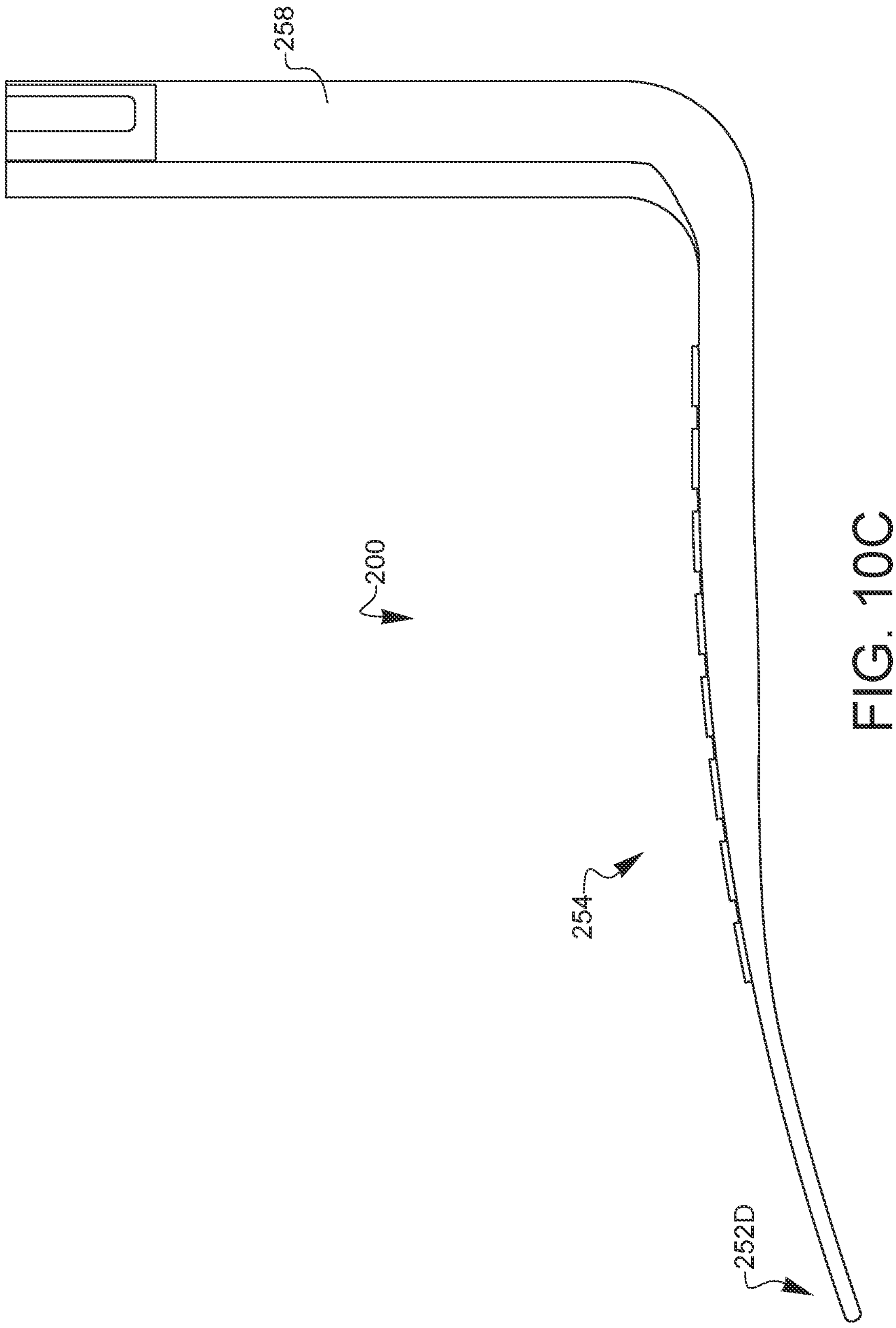
Figure 10E:
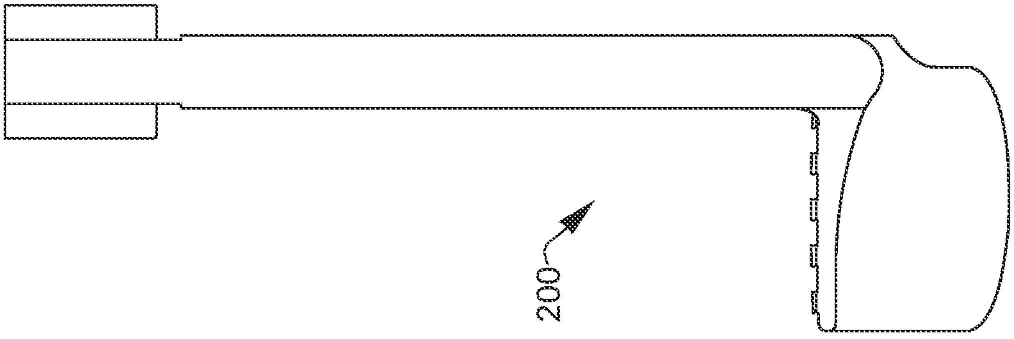
Figure 10D:
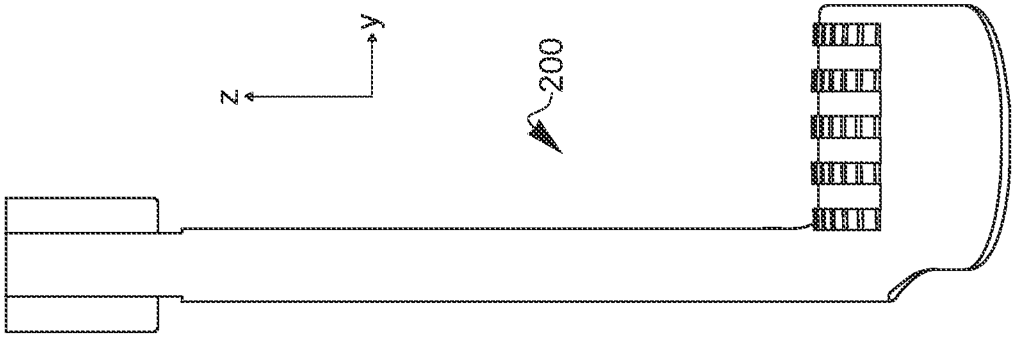
Figure 10F:
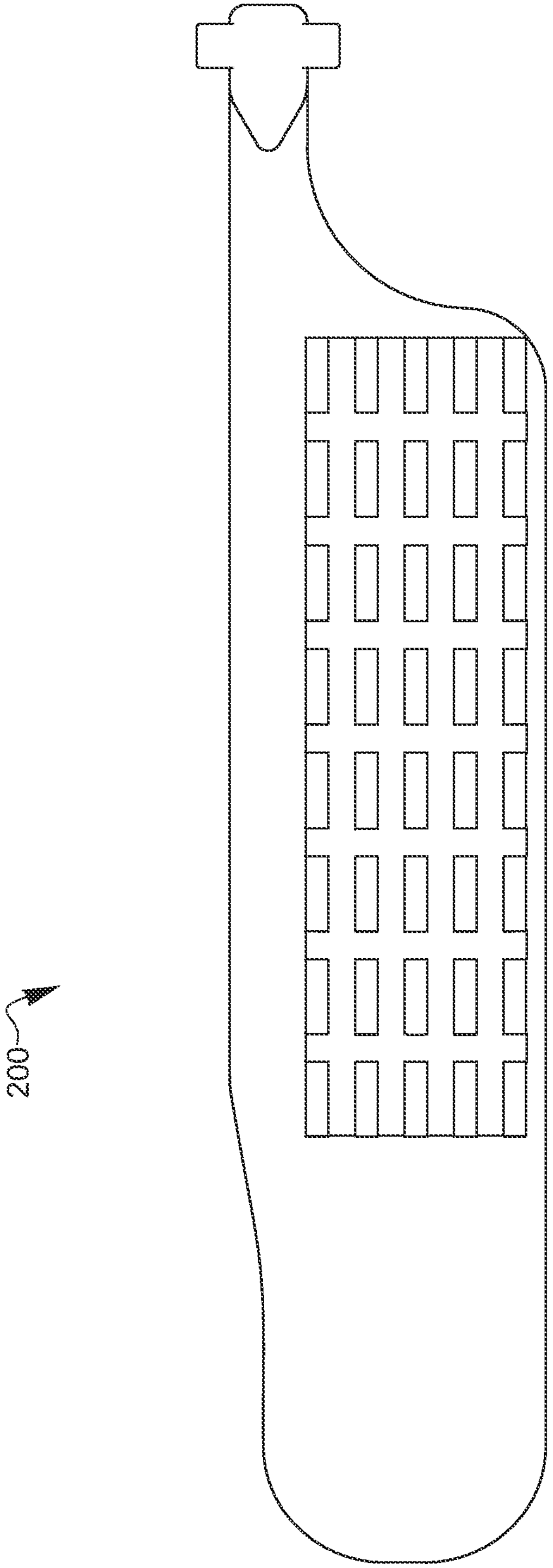
Figure 10G:
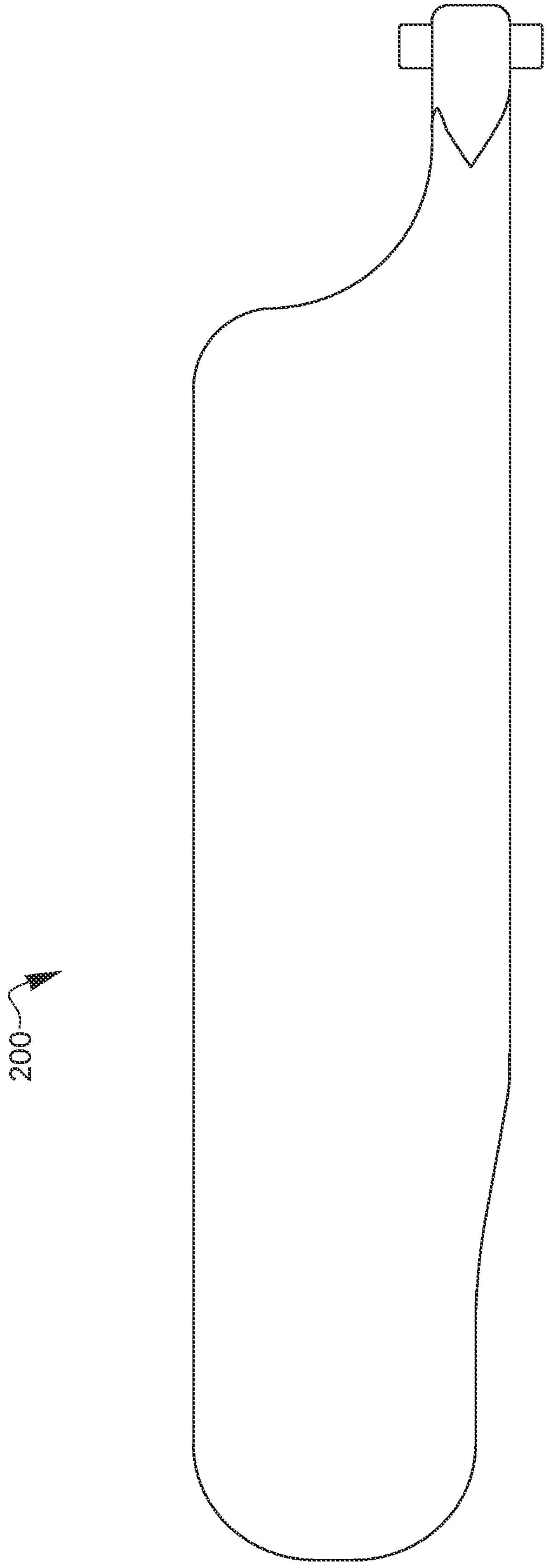

FIGS. 10A to 10G are various views of an embodiment of a right sternal ascender 200. With reference to FIG. 10A, the right sternal ascender 200 defines a panel 254 having several textural features 256, a contralateral, or pertaining to the opposite side of targeted anatomical area, notch 262 at a proximal end 252P, a support beam 260 traversing the underside of the panel 254, and a mounting post 258 for attachment to a sternal ascender apparatus. Turning to FIG. 10B, the panel 254 may extend from a distal end 252D to a panel end 202 along a longitudinal axis 204 that extends generally parallel to the X-axis of the reference coordinate system of FIGS. 10A and 10B. When viewed along the Y-axis of the reference coordinate system of FIG. 10A (or along an axis that is normal to the X-Z plane of the reference coordinate system of FIG. 10B), the panel 254 may be non-planar along all or a portion of the panel 254, as illustrated in FIG. 10B. For example, when viewed along the Y-axis of the reference coordinate system of FIG. 10B, the panel 254 may be curved, arc-shaped, or cambered from the distal end 252D to a panel end 202 or to a point distal to the panel end 202. The curvature of the panel 254 may be constant (i.e., have the shape of a segment of a circle) or may be irregular (may not bend with a constant radius). In some embodiments, a first reference line 253 that is tangent to the curvature of the panel 254 at the panel end 202 may be parallel to the X-axis of the reference coordinate system of FIG. 10B, while a second reference line 255 that is tangent to the curvature of the panel 254 at the distal end 252D may not be parallel to the X-axis of the reference coordinate system of FIG. 10B and may form an angle between 5 degrees and 45 degrees with the X-axis of the reference coordinate system of FIG. 10B. Although a right sternal ascender 200 is illustrated, one having ordinary skill in the art would recognize that an embodiment of a left sternal ascender could have the curved panel 354 illustrated in FIGS. 10A to 10G.

Also defined by the post 258 are two opposing alignment and orientation features 264 configured to align, slide and lock the right sternal ascender 200 into the handle. These features 264 form a general t-shape, which are configured to fit into the aforementioned t-slot on the indicator handle 22. The use of this feature will be identical to that of the left sternal ascender 152 described in regard to FIGS. 7A-7C. The post 258 also defines an angular front alignment feature 266 which is used to help align and place the right sternal ascender 200 in an anatomical notch defined between a rib and sternum. This can serve as a tactile assist in placing the sternal ascender in an appropriate place when in use as part of a sternal ascender apparatus.

FIGS. 11A to 11G are various views of an embodiment of an assembly 300 that includes a sternal ascender apparatus 302 that may be identical to any of the embodiments of the sternal assembly apparatus that has been previously described, such as the embodiments of the sternal ascender apparatus 10 illustrated in FIGS. 1, 8, and 9A to 9D. The assembly 300 may also include a paddle assembly 304 that is coupled to the sternal ascender apparatus 302. Various views of the paddle assembly 304 are illustrated in FIGS. 12A to 12E.

Figure 11A:
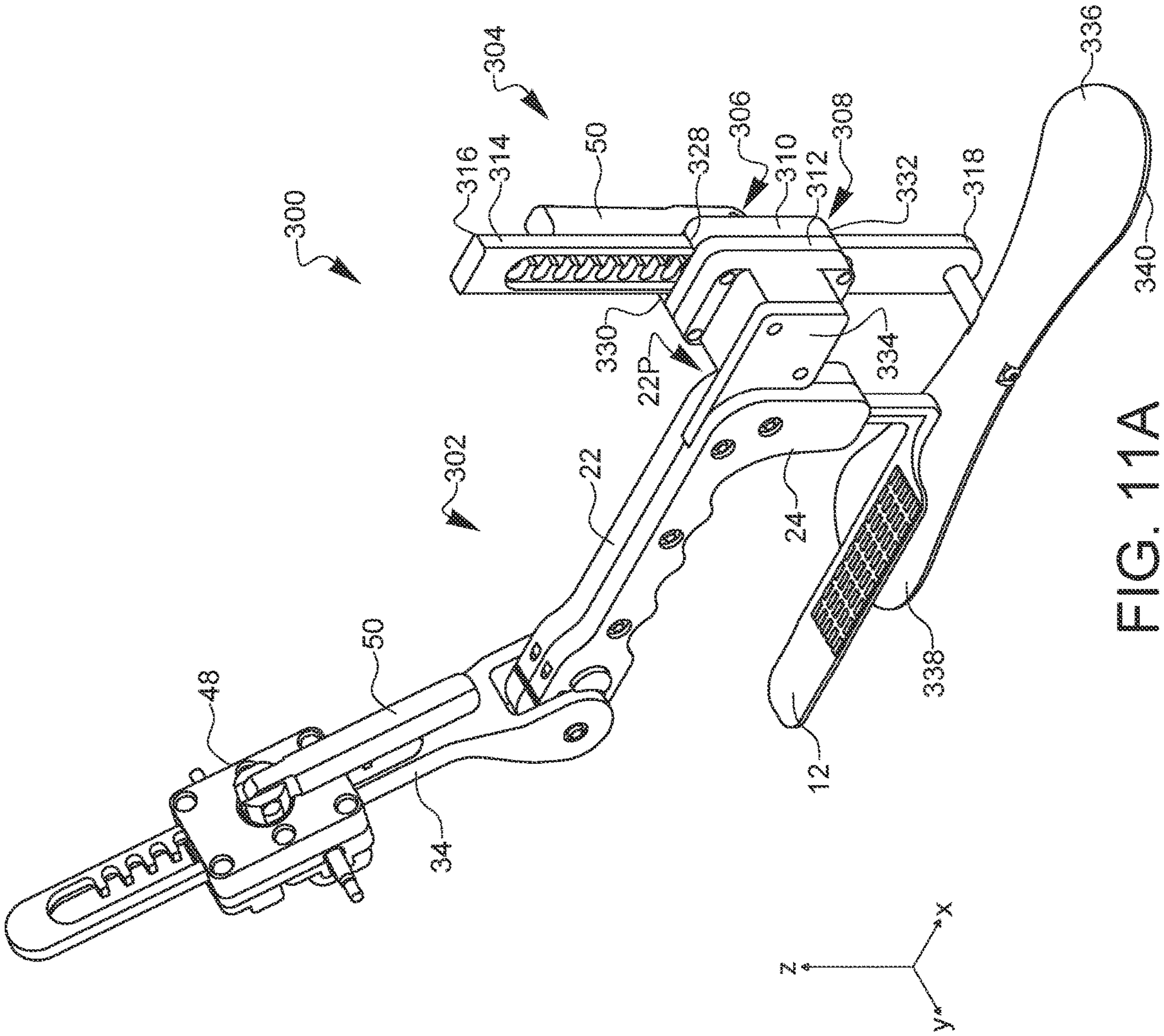
FIGS. 11A to 11G are various views of an embodiment of an assembly including a sternal ascender apparatus and a paddle assembly.
Figure 11B:
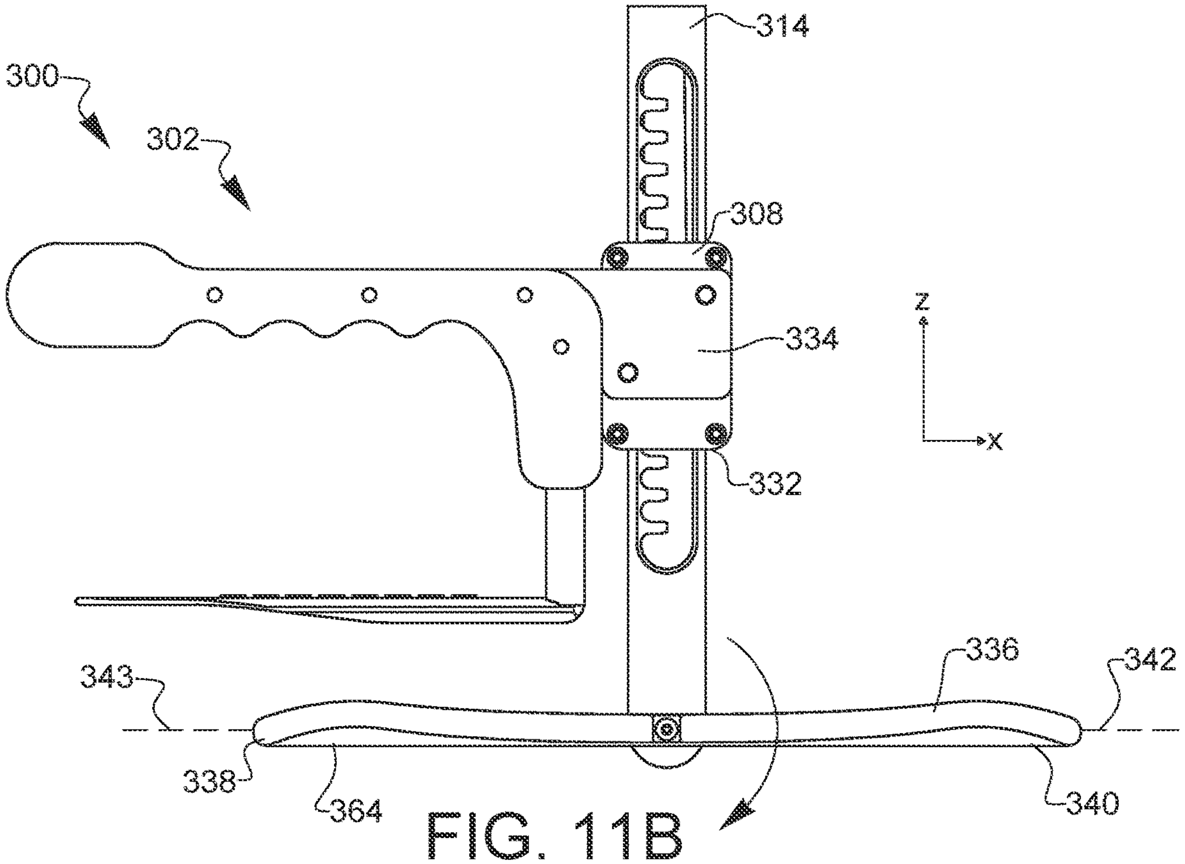

As illustrated in FIG. 11A, the paddle assembly 304 may include a dual side instrument adapter 306 that may be identical or substantially identical to the dual side instrument adapter 44 previously described. The dual side instrument adapter 306 may include a rack housing 308, which may be an assembly of an embodiment of an upper rack housing 310 (which may be identical to the upper rack housing 48 previously described) and a middle rack housing 312 (which may be identical to the middle rack housing 140 previously described). The rack housing 308 may be coupled to a portion of the handle 22 in any suitable manner, such as by a plate 334 extending from a portion of the handle 22 at or adjacent to the proximal end 22P of the handle 22 that is at or adjacent to the mounting portion 24 of the handle 22, and a portion of the rack housing 308 (or the dual side instrument adapter 306) may be fixed or secured to a portion of the plate 334. So configured, the plate 334 may be disposed parallel to the X-Z plane of the reference coordinate system of FIGS. 11A and 11B. However, the rack housing 308 (or the dual side instrument adapter 306) may be fixed, secured, or coupled to a portion of the handle 22 in any other suitable manner.

Figure 14A:
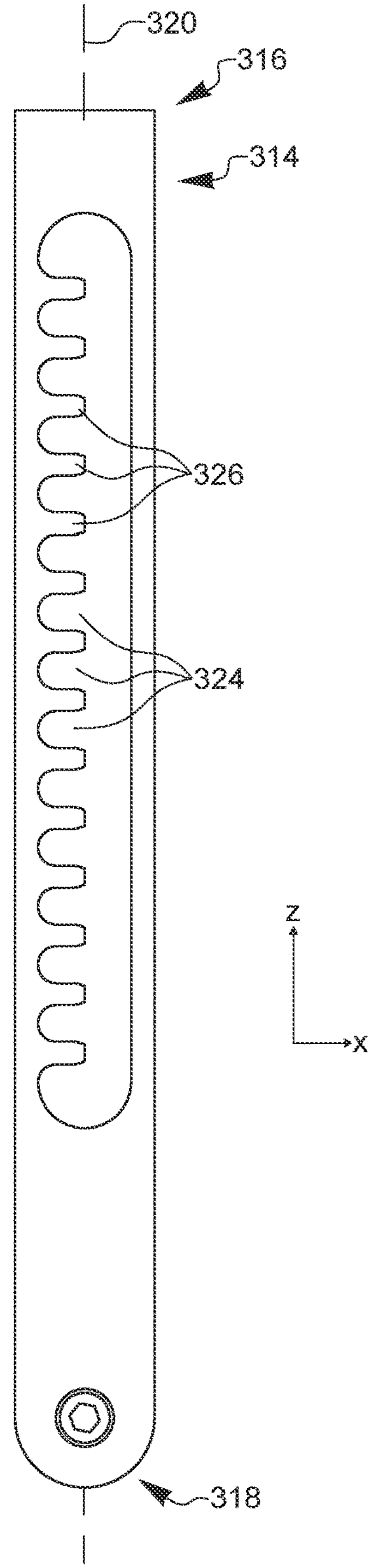
FIGS. 14A to 14B are various views of an embodiment of a support member of the paddle assembly of the assembly of FIGS. 11A to 11G.
Figure 14B:
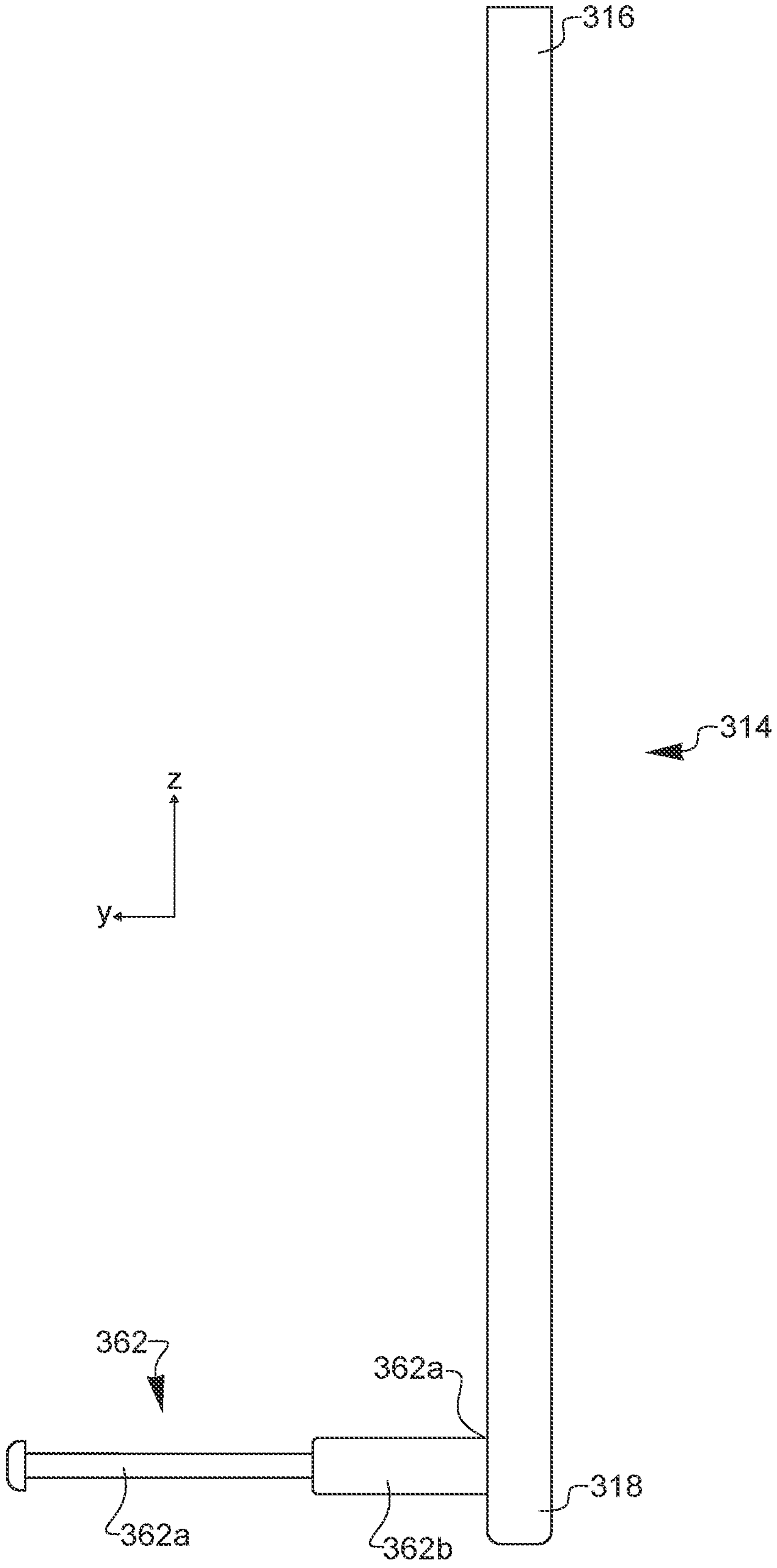

As illustrated in FIG. 11A, the paddle assembly 304 may also include a support member 314, which may be substantially identical to the linear actuator gear 34 previously described. As illustrated in FIGS. 14A and 14B, the support member 314 may extend or generally extend from a first end 316 to a second end 318 along a support member axis 320 that may be parallel to the Z-axis of the reference coordinate system of FIGS. 14A and 14B.

Figure 11C:
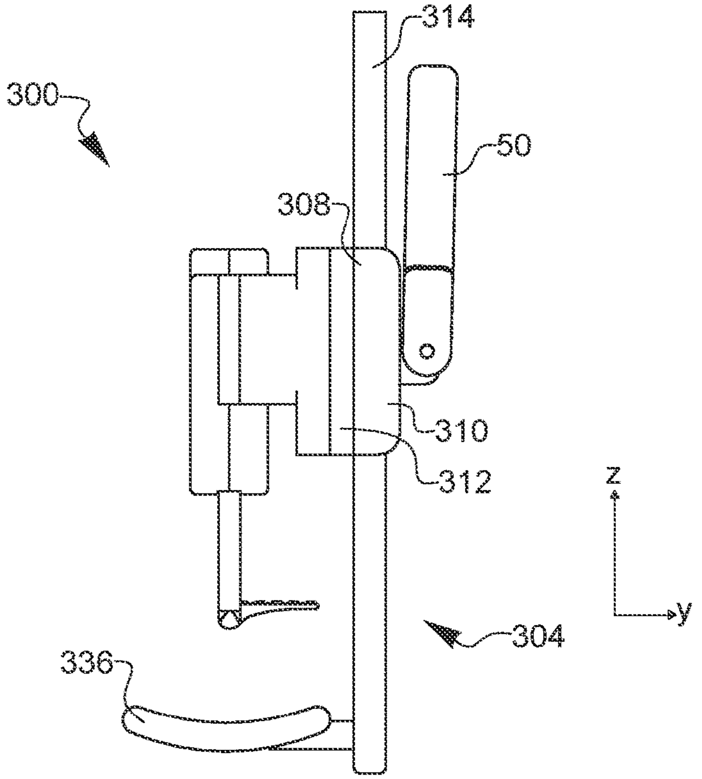
Figure 11D:
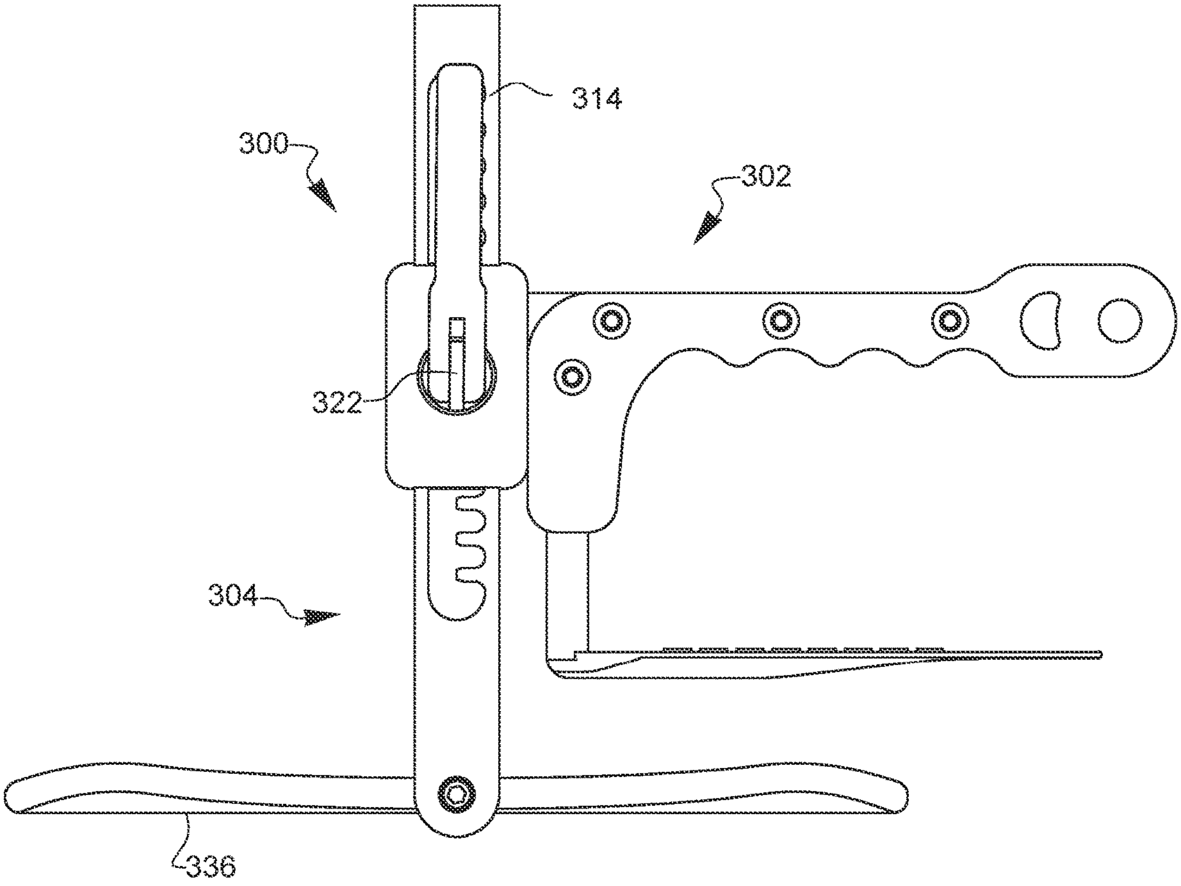
Figure 11E:
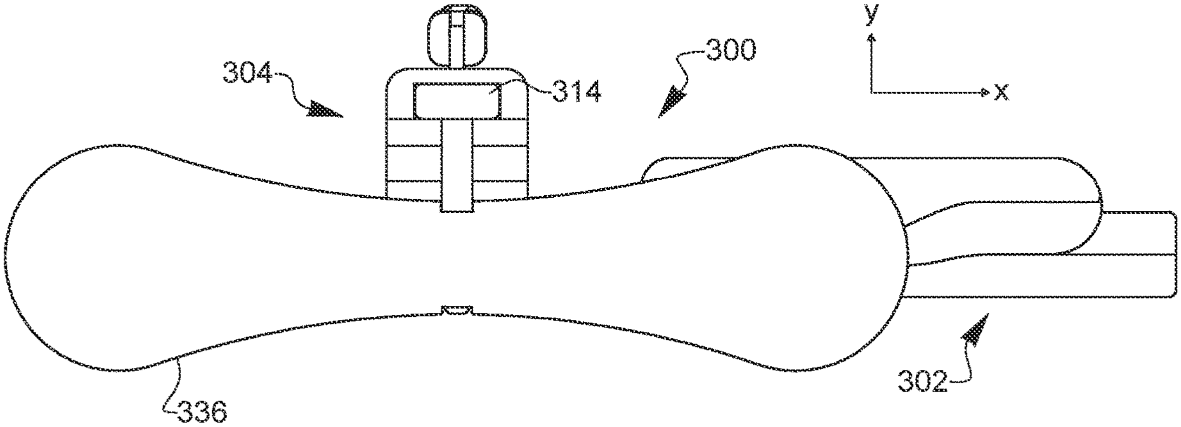
Figure 11F:
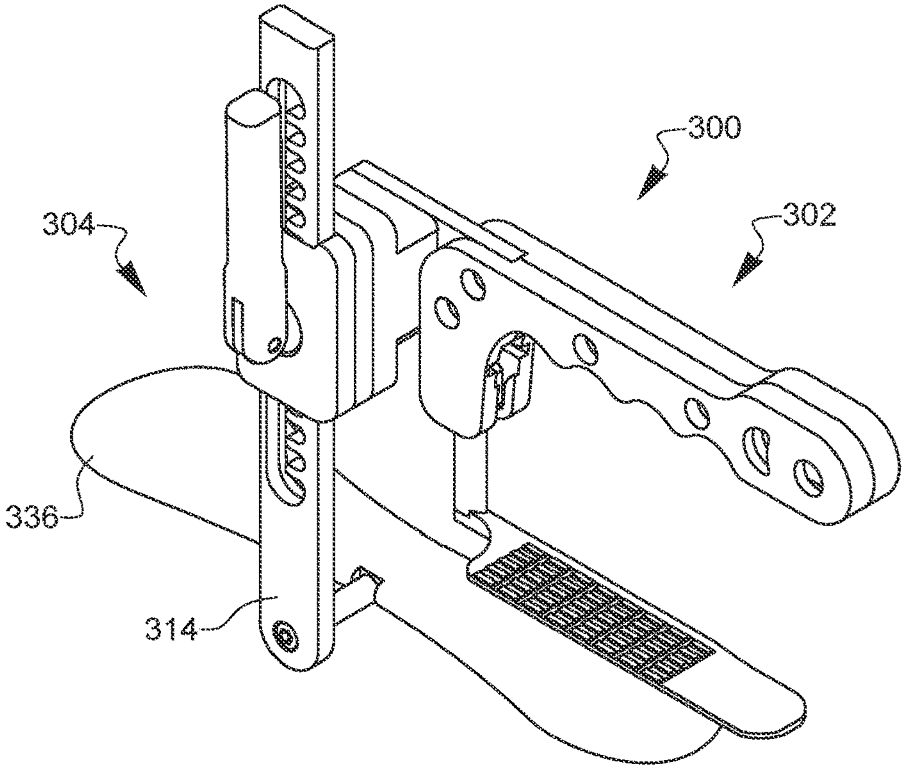
Figure 11G:
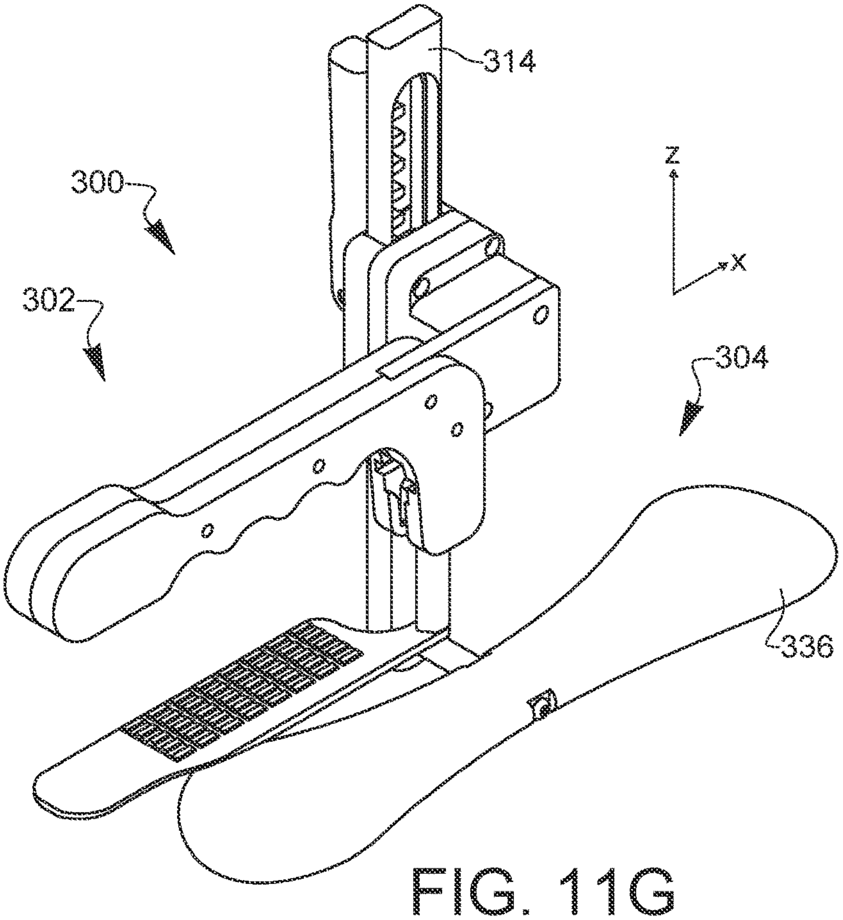
Figure 12A:
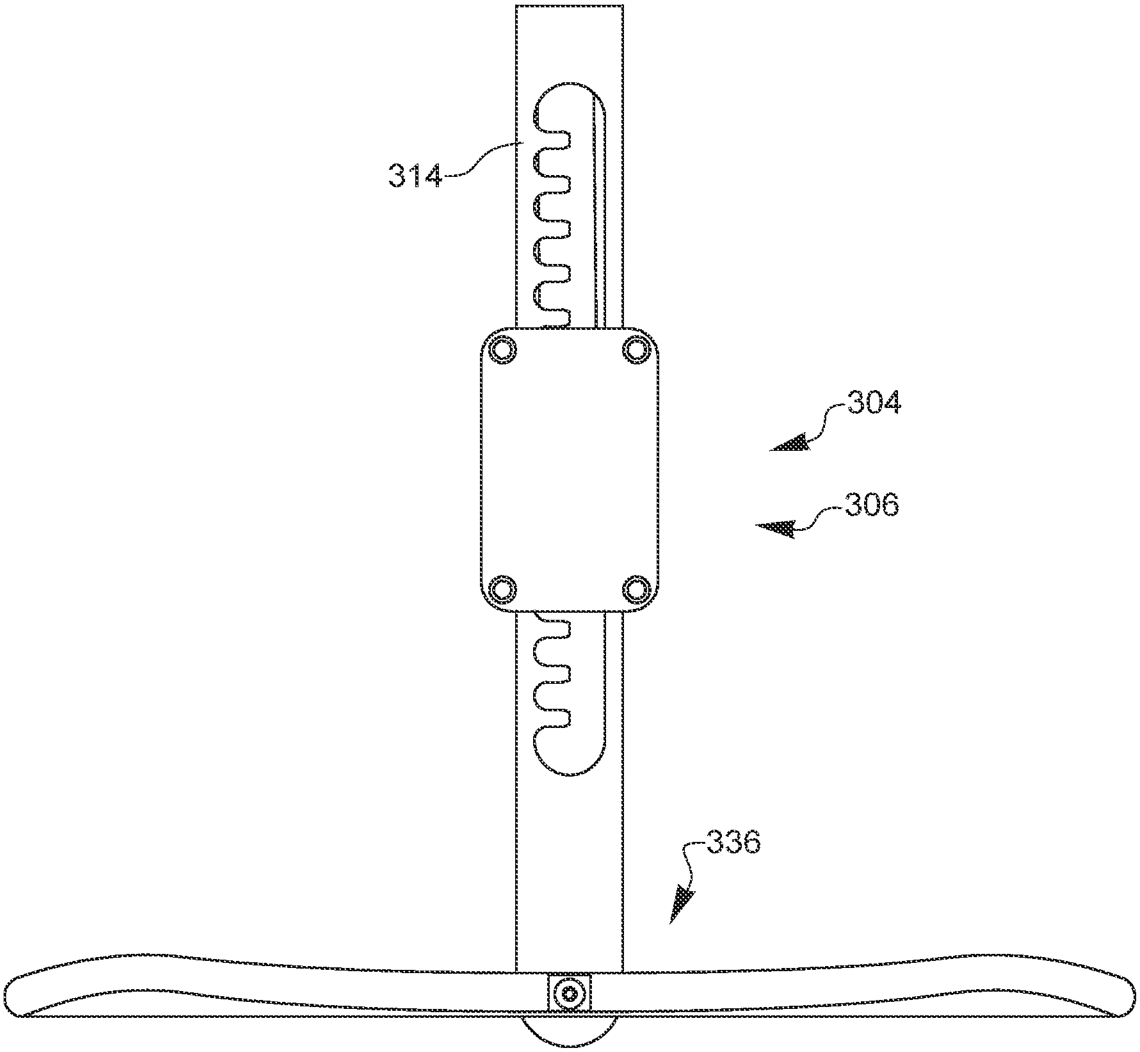
FIGS. 12A to 12E are various views of an embodiment of the paddle assembly of the assembly of FIGS. 11A to 11G.
Figure 12B:
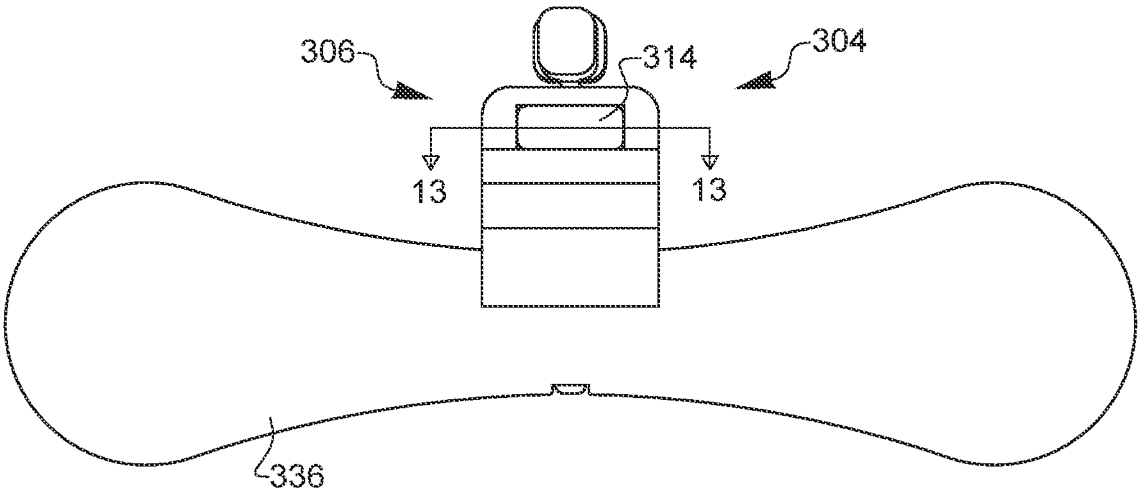
Figure 12C:
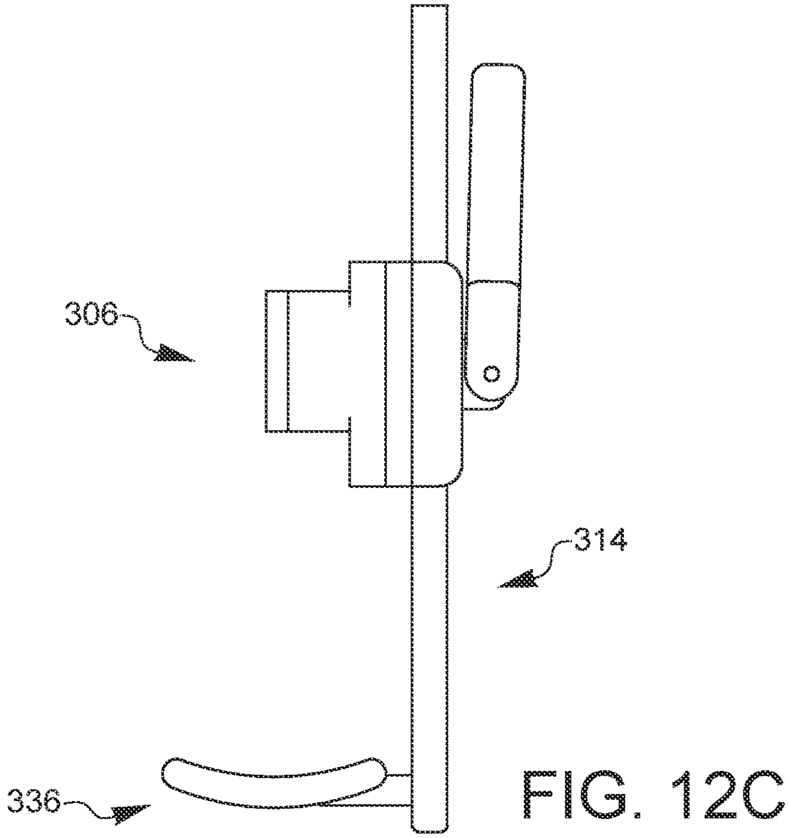
Figure 12D:
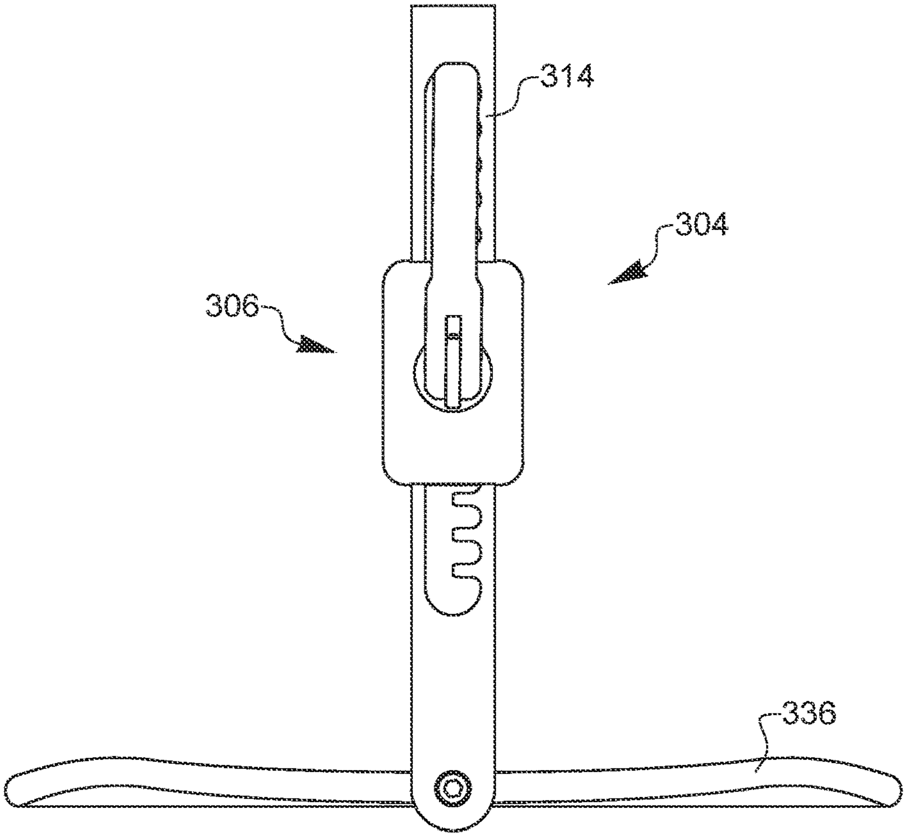
Figure 12E:
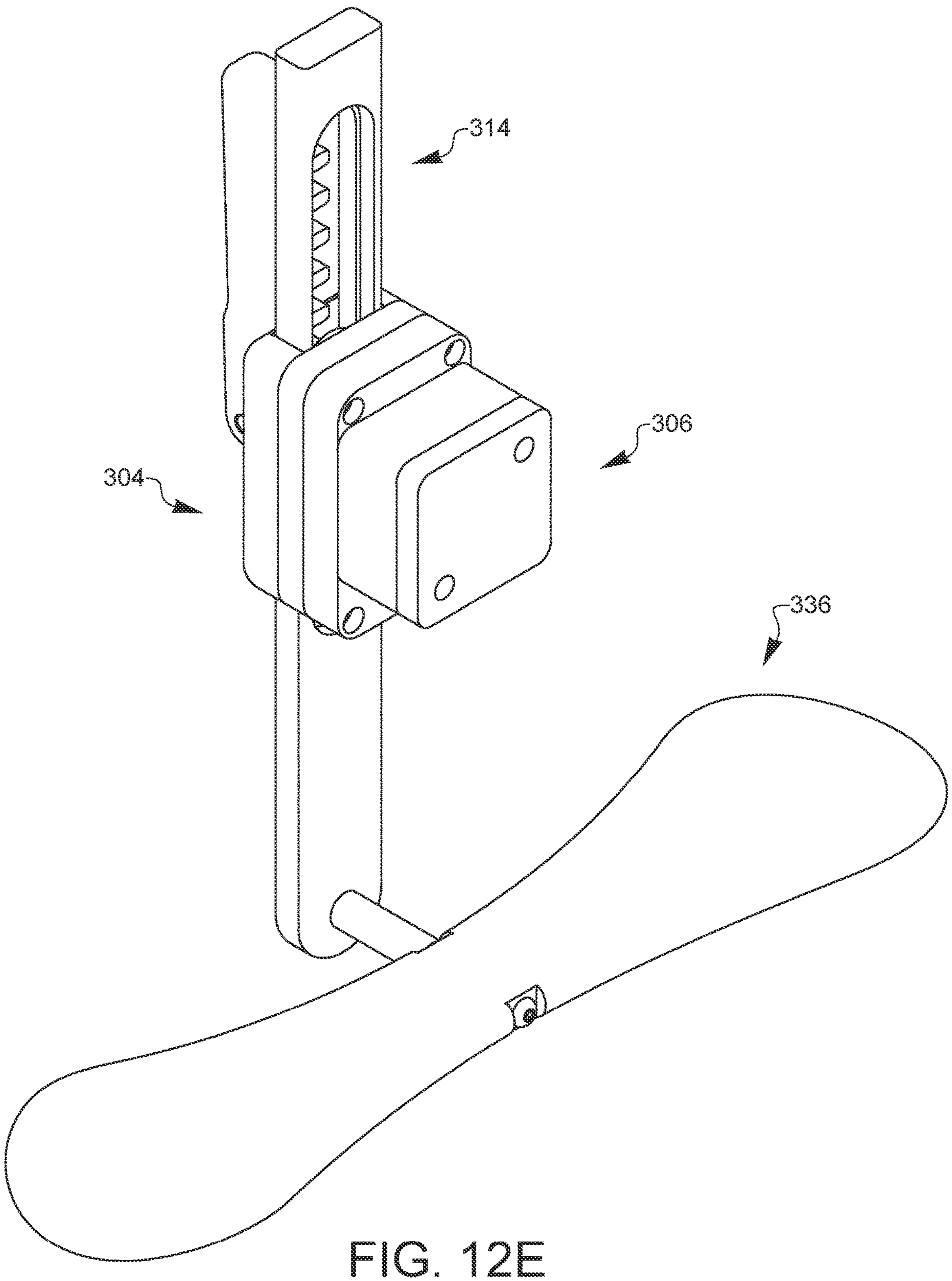
Figure 13:
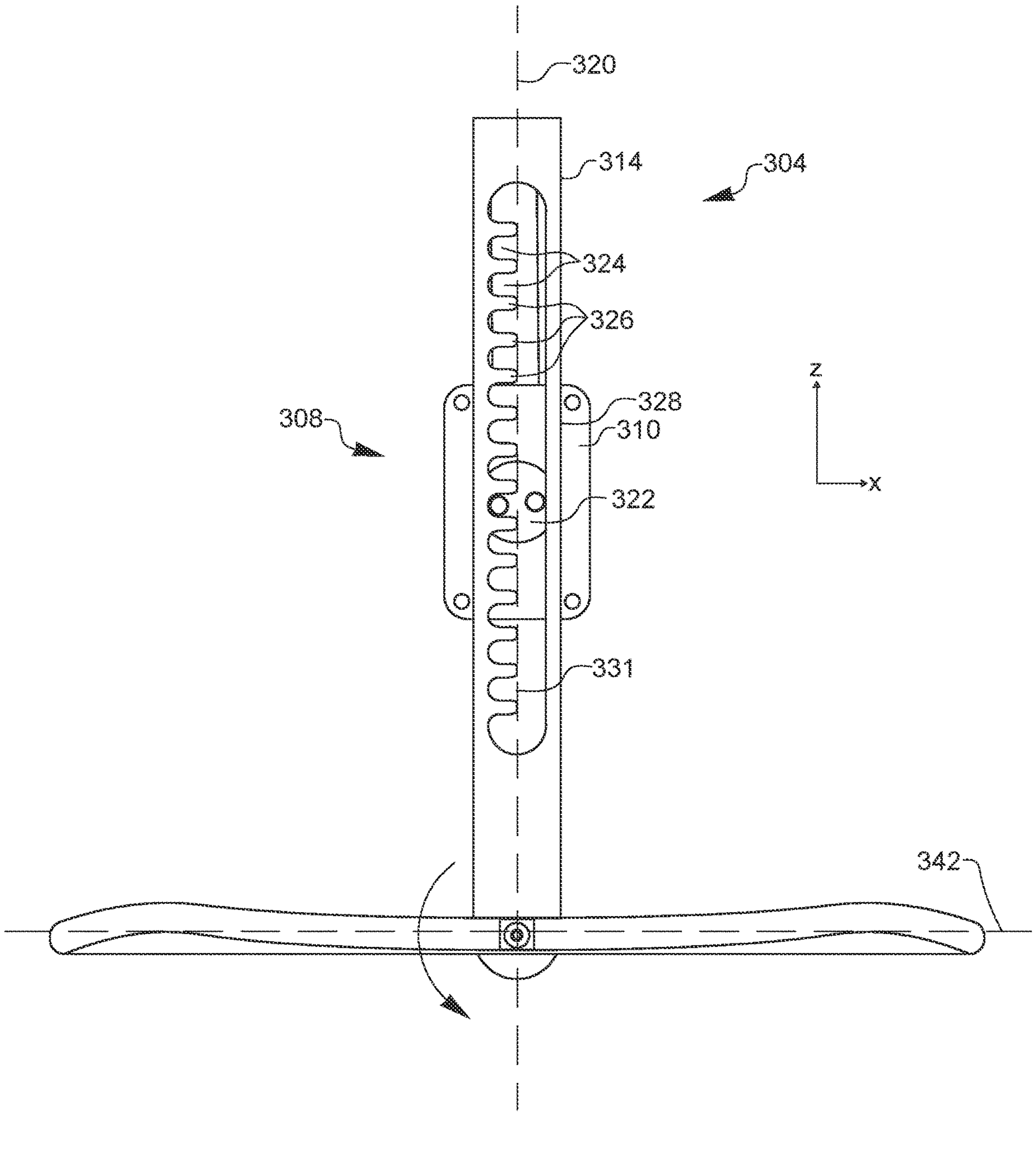
FIG. 13 is a sectional view of the paddle assembly of FIGS. 12A to 12E taken along section line 13-13 of FIG. 12B.

The support member 314 may be coupled to the rack housing 308 in the same manner as the linear actuator housing 34 is coupled to the dual side instrument adapter 44 previously described. That is, with reference to FIG. 11A, a portion of the support member 314 may be slidably disposed within a receiving slot 328 (which may be identical to the actuator slot 42 previously described) of the rack housing 308 that extends through the rack housing 308 along a slot axis 331 (see the sectional view of FIG. 13) from a first end 330 of the rack housing 308 to a second end 332 of the rack housing 308. So disposed, a first post (not shown, but corresponding to post 126 of cylinder gear 122) of a cylinder gear 322 (which is illustrated in FIGS. 11D and 13 and which may be identical to cylinder gear 122 previously described) is disposed within a first recess of the plurality of recesses 324 (which may be identical to recesses 38 previously described) defined by a plurality of teeth 326 (which may be identical to teeth 36 previously described) of the support member 314, which are illustrated in FIGS. 13 and 14A. A second post (not shown, but corresponding to post 126 of cylinder gear 22) of the cylinder gear 322 is disposed within a second recess of the plurality of recesses 324. When the cylinder gear 322 rotates in a first rotational direction about a gear axis (extending through the cylinder gear 322), the first and second posts engage a first portion of the plurality of teeth 326 to displace the linear support member 314 in a first linear direction. When the cylinder gear 322 rotates in a second rotational direction about the gear axis, the first and second posts engage a second portion of the plurality of teeth 326 to displace the support member 314 in a second linear direction.

Figure 15A:
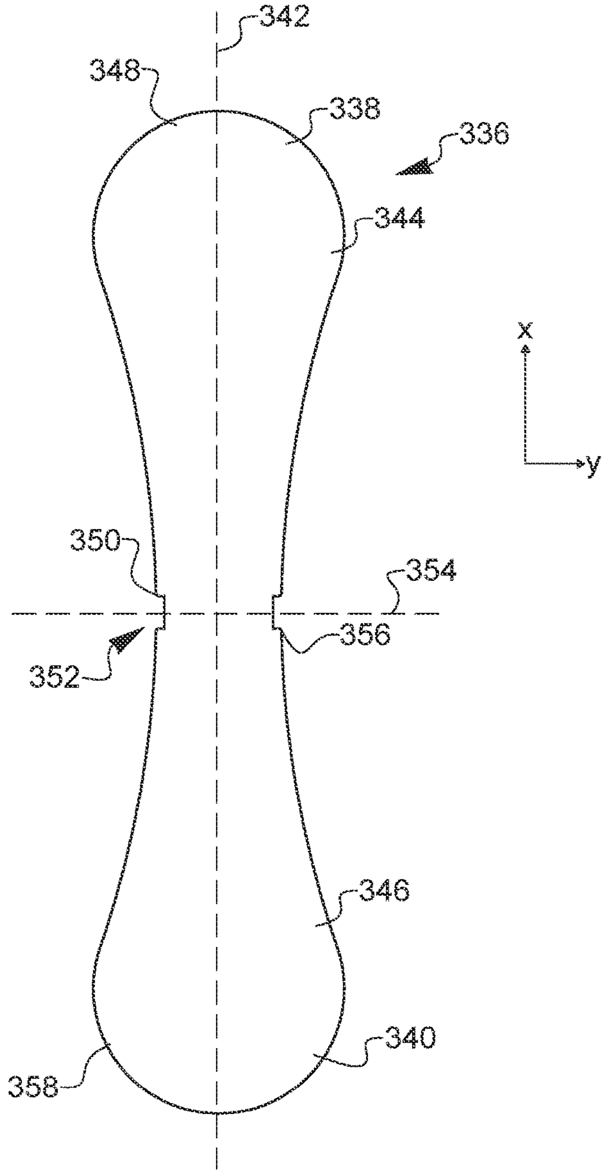
FIGS. 15A to 15B are various views of an embodiment of a paddle member of the paddle assembly of the assembly of FIGS. 11A to 11G.
Figure 15B:
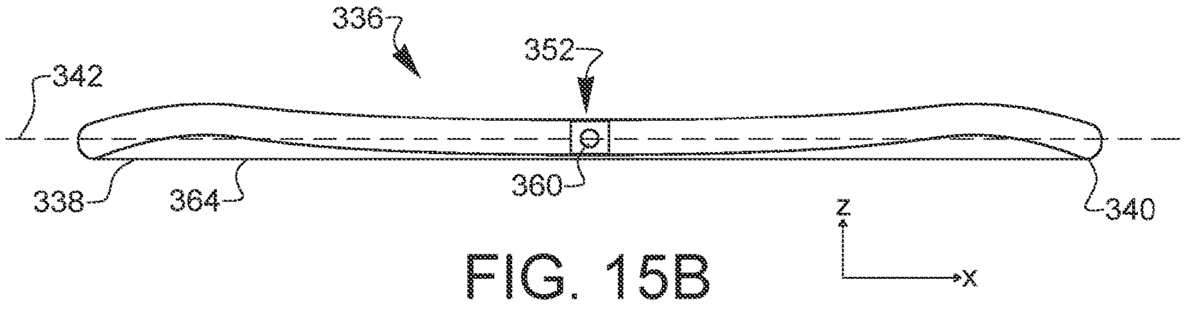

As illustrated in FIG. 11A, the paddle assembly 304 may also include a paddle member 336 coupled to a portion of the support member 314. In some embodiments, the paddle member 336 may be pivotably coupled to the portion of the support member 314, and the portion of the support member 336 may be disposed at or adjacent to the second end 318 of the support member 314. As illustrated in FIGS. 15A, which illustrates a top view of the paddle member 336, the paddle member 336 may extend from a first end 338 to a second end 340 along a paddle axis 342, and the paddle axis 342 may be parallel to the X-axis of the reference coordinate system provided in FIG. 15B, which illustrates a side view of the paddle member 336. The paddle member 336 may have a cambered or arc-shaped cross-sectional shape when viewed along the paddle axis 342 (or the X-axis), as illustrated in FIG. 11C.

With reference to FIG. 15A, the paddle member 336 may include a first longitudinal portion 344 and a second longitudinal portion 346. An intermediate portion 352 may be disposed between the first longitudinal portion 344 and the second longitudinal portion 346 and a pivot axis 354 of the paddle member 336 may extend through the intermediate portion 352 in a direction normal to the paddle axis 342 (i.e., parallel to the Y-axis of the reference coordinate system provided in FIG. 15A). In some embodiments, the pivot axis 354 may be normal to the support member axis 320.

The first longitudinal portion 344 may extend from a first end 348 to a second end 350 along the paddle axis 342. The first end 348 of the first longitudinal portion 344 may corresponds to the first end 338 of the paddle member 336, and the second end 350 of the first longitudinal portion 344 is disposed at or adjacent to the intermediate portion 352 (and/or the pivot axis 354). The second longitudinal portion 346 may extend from a first end 356 to a second end 358 along the paddle axis 342, and the first end 356 of the second longitudinal portion 346 is disposed at or adjacent to the intermediate portion 352 (and/or the pivot axis 354) and the second end 358 of the second longitudinal portion 346 corresponds to the second end 340 of the paddle member 336. The first longitudinal portion 344 may extend a first distance from the first end 348 to the second end 350 along the paddle axis 342, and the second longitudinal portion 346 may extend a second distance from the first end 356 to the second end 358 along the paddle axis 342. In some embodiments, the first distance is equal to or substantially equal to the second distance. However, the first distance may be greater than or less than the second distance.

The paddle member 336 may be pivotably coupled to the support member 314 in any suitable manner. For example, an aperture 360 (illustrated in FIG. 15B) through the intermediate portion 352 of the paddle member 336 may extend along the pivot axis 354 (Illustrated in FIG. 15A), and a first portion 362*a* of a pivot shaft 362 (see FIG. 14B) may be disposed within the aperture 360. Still referring to FIG. 14B, an end portion 362*c* of the pivot shaft 362 may be coupled to a portion of the support member 314 at or adjacent to the second end 318, and a second portion 362*b* of the pivot shaft 362 may be extend between a surface of the support member 314 and the first portion 362*a* of a pivot shaft 362 such that the intermediate portion 352 of the paddle member 336 (illustrated in FIG. 15A) is offset from the surface of the support member 314 in a direction along the Y-axis of the reference coordinate system provided in FIG. 14B. So configured, the paddle member 336 may rotate or pivot about the pivot axis 354 relative to the support member 314. The paddle member 336 may rotate or pivot about the pivot axis 354 a full 360 degrees or any suitable angular range. For example, the paddle member 336 may rotate or pivot about the pivot axis 354 at least 45 degrees above and below fixed reference line 343 that is parallel to the X-axis of the reference coordinate system provided in FIG. 11B (i.e., such that the paddle axis 342 forms an angle of 45 degrees or less relative to the fixed reference line 343 that is parallel to the X-axis of the reference coordinate system provided in FIG. 11B when rotated either clockwise or counterclockwise). The paddle member 336 may freely rotate about the pivot axis 354 or may have a lock or stop (such as a frictional lock or stop) to retain the paddle member 336 in a desired rotational position, or in any one of a plurality of predefined rotational positions. The lock may be manually operated, or may be automatically engaged by rotation of the paddle member 336.

Figure 16A:
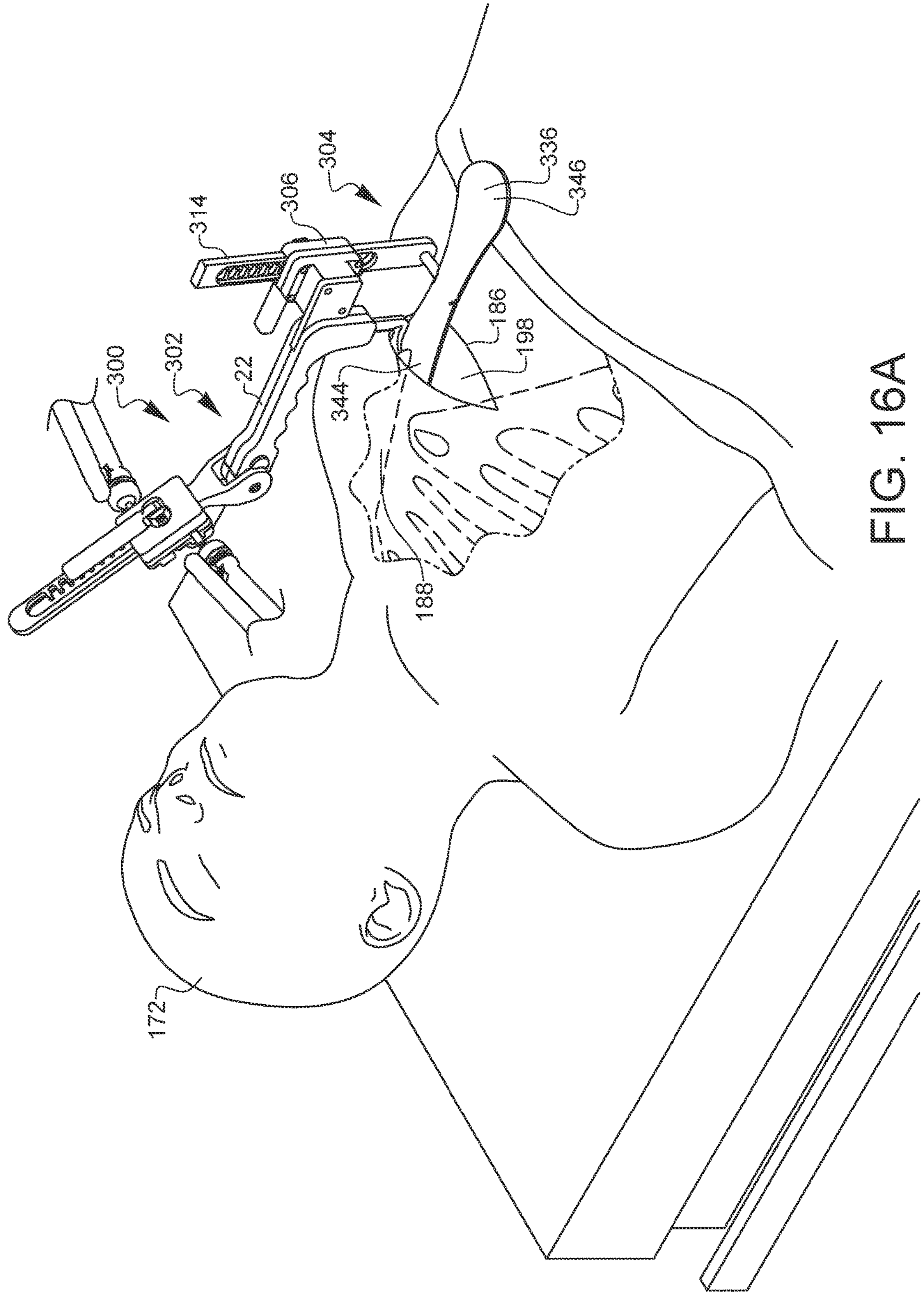
FIGS. 16A to 16C are a series of perspective views illustrating operational steps of the use of the assembly of FIGS. 11A to 11G in a surgical context.
Figure 16B:
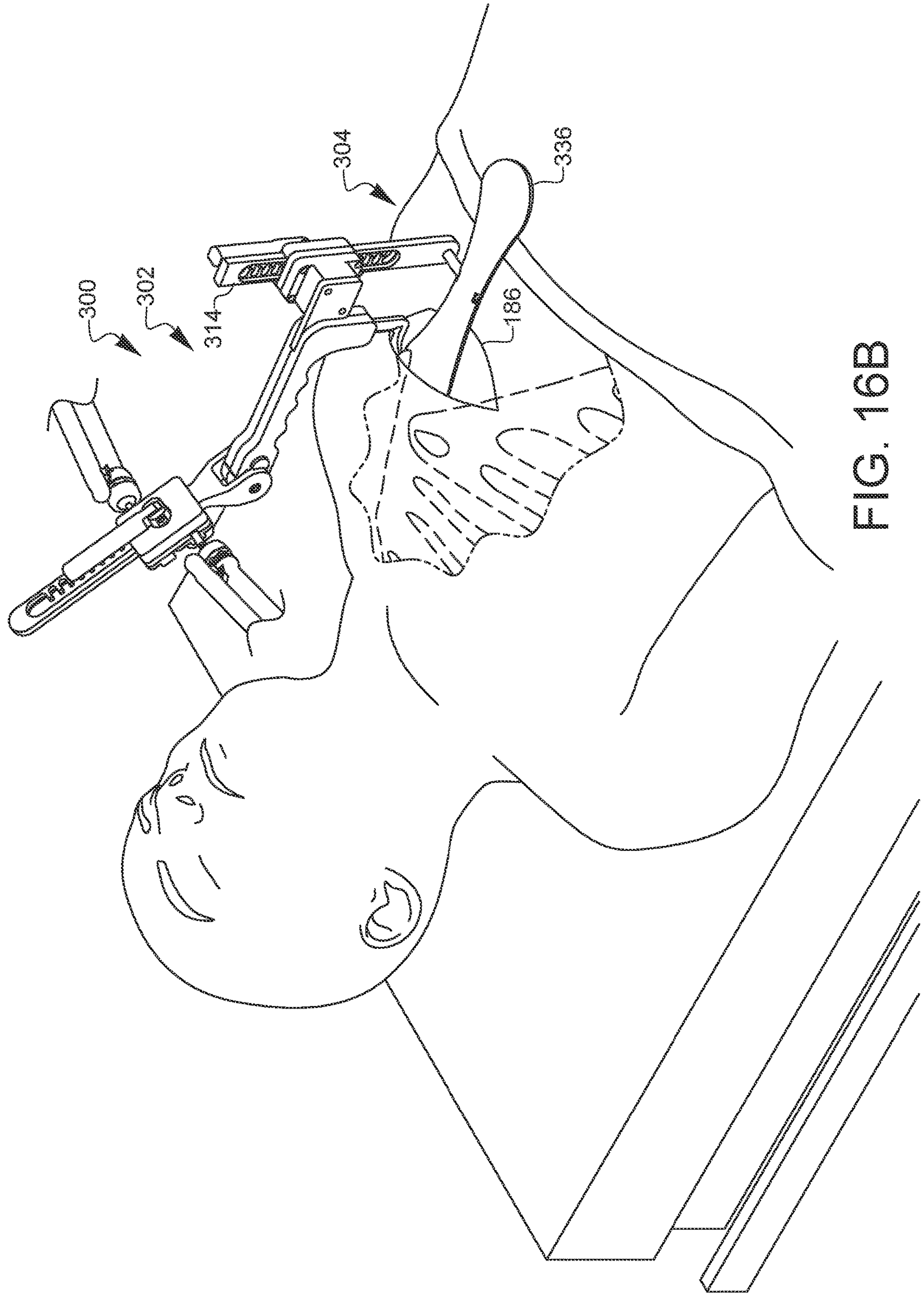
Figure 16C:
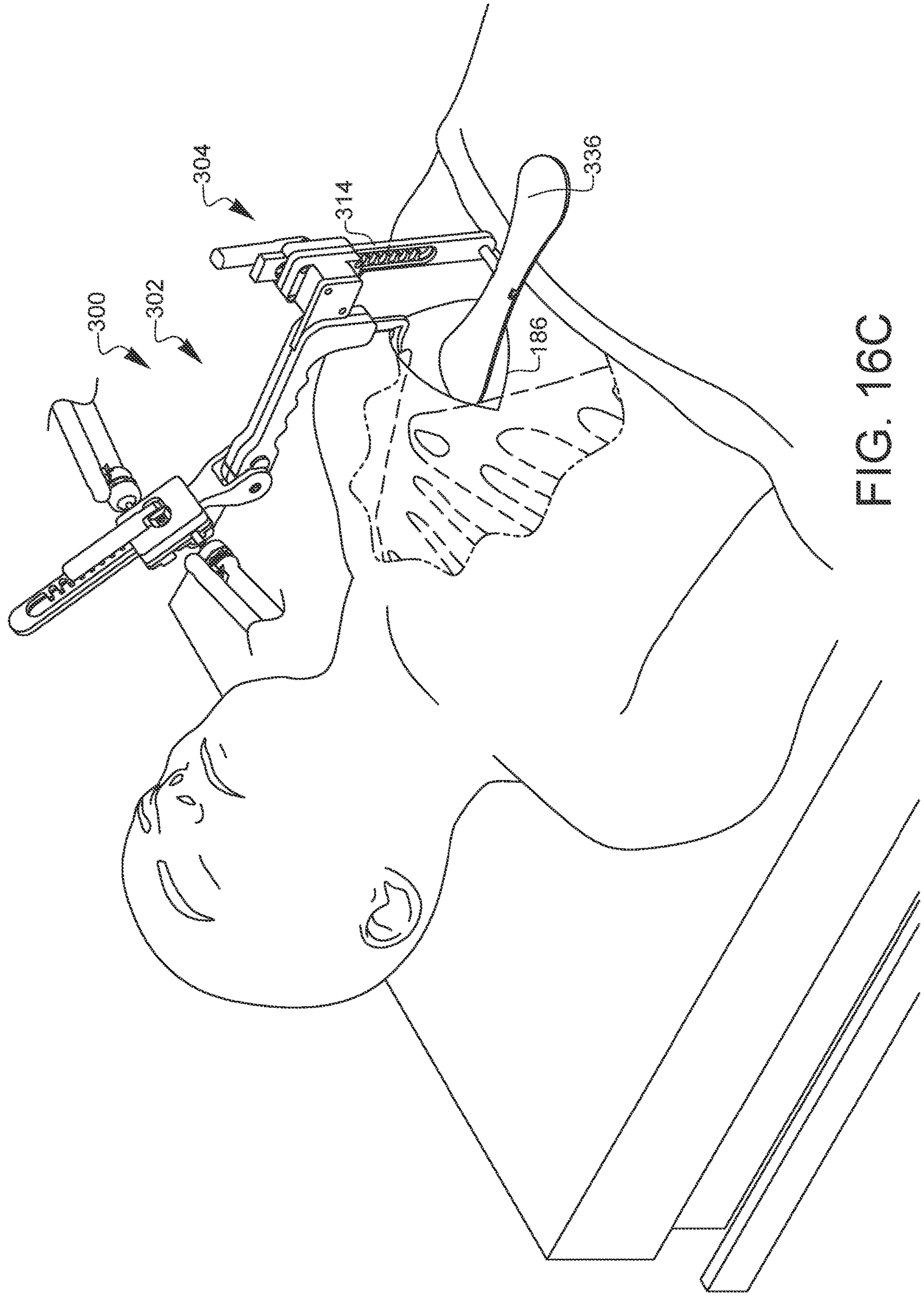

So configured, when the assembly is used in a surgical procedure such as that illustrated in FIGS. 16A to 16C, the sternal ascender apparatus 302 of the assembly 300 may be used as previously described (e.g., in the procedure illustrated in FIGS. 8 and 9A to 9D) to apply retraction to the sternum 188 of the patient 172 and create the subxiphoid space 198 for access by a surgeon. In such a procedure, the paddle assembly 304 secured to the embodiment of the sternal ascender apparatus 302 may be used to create more subxiphoid space 198 to further improve access for the surgeon. Specifically, all or a portion of the first longitudinal portion 344 of the paddle member 336 may be placed inside the incision 188. The handle 50 (illustrated in FIG. 11A) of the paddle assembly 304 may be rotated in a first rotational direction to displace the support member 314 in a first linear direction (i.e., along or parallel to the Z-axis of the reference coordinate system provided in FIG. 11A such that the second end 318 of the support member 314 is displaced away from the second end 332 of the rack housing 308). As the support member 314 continues to be displaced in the first linear direction, a bottom surface 364 (see FIG. 15B) of the first longitudinal portion 344 may contact portions of the patient's 172 inner organs and apply pressure to the inner organs as the support member 314 continues to be displaced in the first linear direction. The paddle member 336 may pivot about the pivot axis 354 (see FIG. 15A) due to contact with the inner organs while the first longitudinal portion 344 is displaced into contact with the inner organs. Optionally, the second longitudinal portion 346 may be rotated by the surgeon about the pivot axis 354 to apply further pressure to the inner organs using the first longitudinal portion 344. Regardless, pressure to the patient's inner organs applied by the first longitudinal portion 344 of the paddle member 336 may compress the organs, thereby creating additional subxiphoid space 198 adjacent to the incision 186 for the surgeon. Further, or alternatively, if the patient 172 is obese, all or a portion (e.g., the second longitudinal portion 346) of the paddle member 336 may contact portions of the patient's body 172 outside (or inside) of the incision 186 to compress fat stores that may obstruct access thorough the incision 186.

Various advantages of a sternal ascender assembly have been discussed above. Embodiments discussed herein have been described by way of example in this specification. It will be apparent to those skilled in the art that the foregoing detailed disclosure is intended to be presented by way of example only, and is not limiting. As just one example, although the end effectors in the discussed examples were often focused on the use of a scope, such systems could be used to position other types of surgical equipment. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. An assembly comprising:

a handle portion;

a fixed lifting member directly coupled to a first portion of the handle portion, the fixed lifting member configured to be inserted into a first portion of sub-xiphoid incision of a patient by a user;

a rack housing coupled to a second portion of the handle portion, the rack housing having a receiving slot that extends through the rack housing along a slot axis from a first end of the rack housing to a second end of the rack housing, and wherein a cylinder gear is movably coupled to the rack housing, wherein the handle portion does not rotate relative to the rack housing;

a support member that extends from a first end to a second end along a support member axis, wherein a portion of the support member is slidably disposed within the receiving slot, and wherein the cylinder gear operatively engages a portion of the first portion of the support member to displace the support member relative to the rack housing;

a paddle member pivotably coupled to a first portion of the support member, wherein the paddle member pivots about a pivot axis, wherein the paddle member extends from a first end to a second end along a paddle axis, and wherein the pivot axis extends transversely through an intermediate portion of the paddle, wherein the paddle member is configured to be inserted into a second portion of sub-xiphoid incision of a patient by a user such that a surface of the paddle member is contact with a portion of the patient's inner organs to create space within the sub-xiphoid incision when the paddle member is displaced in a first direction.

2. The assembly of claim 1, wherein the pivot axis is normal to the support member axis.

3. The assembly of claim 1, wherein the paddle member includes a first longitudinal portion and a second longitudinal portion, wherein the first longitudinal portion extends from a first end to a second end along the paddle axis, and wherein the first end of the first longitudinal portion corresponds to the first end of the paddle member and the second end of the first longitudinal portion is disposed at or adjacent to the intermediate portion of the paddle member, and wherein the second longitudinal portion extends from a first end to a second end along the paddle axis, and wherein the first end of the second longitudinal portion is disposed at or adjacent to the intermediate portion of the paddle member and the second end of the second longitudinal portion corresponds to the second end of the paddle member.

4. The assembly of claim 3, wherein the first longitudinal portion extends a first distance from the first end to the second end along the paddle axis, and wherein the second longitudinal portion extends a second distance from the first end to the second end along the paddle axis.

5. The assembly of claim 4, wherein the first distance is equal to the second distance.

6. The assembly of claim 1, wherein the rack housing is fixedly coupled to the handle portion.

7. The assembly of claim 1, wherein the slot axis is parallel to the support member axis.

* * * * *